United States Patent
Mignon Godefroy et al.

(10) Patent No.: US 9,103,828 B2
(45) Date of Patent: Aug. 11, 2015

(54) **METHOD FOR DIAGNOSING *STREPTOCOCCUS, ENTEROCOCCUS* AND *PEPTOSTREPTOCOCCUS* GENERA INFECTIONS**

(75) Inventors: Karine Yvonne Gabrielle Mignon Godefroy, Paris (FR); Hélène Nuyttens, Ivry sur Seine (FR); Julie Roge, Montrouge (FR); Damien Yann Marie-Joseph Thomas, Chilly Mazarin (FR)

(73) Assignee: Diaxonhit, Paris (FR)

( * ) Notice: Subject to any disclaimer, the term of this patent is extended or adjusted under 35 U.S.C. 154(b) by 49 days.

(21) Appl. No.: 13/571,541

(22) Filed: Aug. 10, 2012

(65) Prior Publication Data

US 2013/0040321 A1    Feb. 14, 2013

Related U.S. Application Data

(60) Provisional application No. 61/522,522, filed on Aug. 11, 2011.

(30) Foreign Application Priority Data

Aug. 11, 2011    (EP) .................................... 11306037

(51) Int. Cl.
*G01N 33/569*    (2006.01)

(52) U.S. Cl.
CPC .... *G01N 33/56944* (2013.01); *G01N 2333/315* (2013.01); *G01N 2469/10* (2013.01)

(58) Field of Classification Search
None
See application file for complete search history.

(56) References Cited

U.S. PATENT DOCUMENTS

| 2003/0138775 A1* | 7/2003 | Le Page et al. .................... 435/6 |
| 2006/0210581 A1* | 9/2006 | Telford et al. .............. 424/190.1 |
| 2009/0104218 A1 | 4/2009 | Tettelin et al. |

FOREIGN PATENT DOCUMENTS

WO    02092818 A2    11/2002

OTHER PUBLICATIONS

Greenspan et al. Nature Biotechnology 17:936-937, 1999.*
Skolnick et al. Trends in Biotechnology 18: 34-39, 2000.*
McGuinness et al. Lancet 337: 514-517, 1991.*
McGuinness et al. Mol. Microbiol. 7: 505-514, 1993.*
Schäfer et al., "Prolonged Bacterial Culture to Identify Late Periprosthetic Joint Infection: A Promising Strategy", Clinical Infectious Diseases, Dec. 1, 2008, pp. 1403-1409, vol. 47, No. 11.
Extended European Search Report for corresponding EP Application No. 11306037.0, 10 pages.

* cited by examiner

*Primary Examiner* — S. Devi
(74) *Attorney, Agent, or Firm* — Thompson Coburn LLP

(57) ABSTRACT

The invention concerns a method to determine if an individual is infected by a bacterium selected from the group consisting *Streptococcus, Enterococcus* and *Peptostreptococcus* genera comprising: (i) detection of antibodies directed against at least one protein of sequence SEQ ID NO: 2, SEQ ID NO: 4, SEQ ID NO: 6 or SEQ ID NO: 8, in a biological sample of the individual, and (ii) deducing therefrom that the individual is infected by a bacterium selected from the group consisting of *Streptococcus, Enterococcus* and *Peptostreptococcus* genera. The invention further concerns the kit for diagnosing of such an infection.

9 Claims, No Drawings

METHOD FOR DIAGNOSING STREPTOCOCCUS, ENTEROCOCCUS AND PEPTOSTREPTOCOCCUS GENERA INFECTIONS

CROSS REFERENCE TO RELATED APPLICATIONS

This application claims the benefit of U.S. Provisional Application No. 61/522,522, filed Aug. 11, 2011, and claims priority under 35 USC §119 to European patent application EP 11306037.0, filed Aug. 11, 2011, both of which are incorporated herein by reference in their entireties.

INCORPORATION OF SEQUENCE LISTING

A Sequence Listing containing the file named "12P1873_SEQLIST_ST25.txt" which is 83,782 bytes (as measure in MS-Windows®) and created on Aug. 9, 2012, is incorporated herein by reference in its entirety. The Sequence Listing contains SEQ ID NOs: 1-24.

FIELD OF THE INVENTION

The invention concerns a method for determining if an individual is infected by a bacterium selected from the group consisting of Streptococcus, Enterococcus and Peptostreptococcus genera comprising: (i) detection of antibodies directed against at least one protein of sequence SEQ ID NO: 2, SEQ ID NO: 4, SEQ ID NO: 6 or SEQ ID NO: 8, in a biological sample of the individual, and (ii) deducing therefrom that the individual is infected by a bacterium selected from the group consisting Streptococcus, Enterococcus and Peptostreptococcus genera. The invention further concerns the kit for diagnosing of such an infection.

BACKGROUND OF THE INVENTION

Viridans streptococci and the β-hemolytic streptococci constitute a diverse group of organisms with varying environmental niches and pathogenicity. Although these organisms reside as commensals in the respiratory and intestinal tracts of humans, they may also invade sterile body sites, resulting in life-threatening diseases.

Viridans streptococci such as S. mitis group consisting of S. mitis, S. sanguis, S. gordonii, S. oralis are an important part of the normal microbial flora of humans. They are indigenous to the upper respiratory tract, the female genital tract, and all regions of the gastrointestinal tract, but are most prevalent in the oral cavity. They are responsible for bacteremia with 2.6% of positive blood cultures reported from clinical laboratories, for meningitis accounting for 0.3% to 5% of culture-proven cases, for pneumonia even if often isolated with non clinical significance, and miscellaneous infections such as pericarditis, peritonitis, acute bacterial sialadenitis, orofacial odontogenic infections, endophtalmitis, spondylodiscitis, and various upper respiratory tract infections (otitis, media, sinusitis).

Beta-hemolytic streptococci of large colony size (0.5 mm in diameter) can be grouped with Lancefield antisera using latex agglutination or coagglutination directed against the cell wall carbohydrate of groups A, B, C, or G. Infections caused by these groups are often severe: pneumonia, pharyngitis, arthritis with 11% to 28% of cases, osteomyelitis, endocarditis, respiratory tract infections, endocarditis, meningitis, puerperal infection, neonatal sepsis, bacteremia, skin and soft tissue infections (cellulitis, foot ulcers, abscess), infections of the female genital tract (group B streptococci) and other miscallenous infections such as pericarditis, pyomyositis, purpura, and spinal epidural abscess (Mandell, Douglas and Bennett's: Principles and practice of infectious Disesases, Sixth ed., volume 1).

Because enterococci are part of the normal gut flora of almost all humans, they are capable of causing infections both in and out of the hospital setting. Most enterococcal infections, however, occur in hospitalized patients or patients undergoing therapy such as peritoneal or hemodyalisis. Currently, enteroccocci infections rank second or third in frequency as causes of nosocomial infections in the United-States. Risk factors for acquiring nosocomial enterococcal infections include gastrointestinal colonization; serious underlying disease; a long hospital stay; prior surgery; renal insufficiency; neutropenia; transplantation (especially liver and bone marrow), the presence of urinary or vascular catheters; and residency in an intensive care unit. Clinical infections caused by enterococci are urinary tract infections, bacteremia, endocarditis, intra-abdominal and pelvic infections, wound and tissue infections, meningitis, respiratory tract infections and neonatal sepsis (Mandell, Douglas and Bennett's: Principles and practice of infectious Disesases, Sixth ed., volume 1).

Peptostreptococcus species are commensal organisms in humans, living predominantly in the mouth, skin, gastrointestinal, and urinary tracts, and compose a portion of the bacterial gut flora. Under immunosuppressed or traumatic conditions these organisms can become pathogenic, as well as septicemic, harming their host. Peptostreptococcus can cause brain, liver, breast, and lung abscesses, as well as generalized necrotizing soft tissue infections. They participate in mixed anaerobic infections, a term which is used to describe infections that are caused by multiple bacteria. These different bacterial species raise the problem of their detection in human pathological specimens and of their identification when isolated from such samples (Mandell, Douglas and Bennett's: Principles and practice of infectious Disesases, Sixth ed., volume 1).

Patients receiving total joint replacements number in the hundreds of thousands each year worldwide, and millions people have indwelling prosthetic articulations. Between 1 and 5% of indwelling prostheses become infected; this is a calamity for the patient, and it is associated with significant morbidity and occasionally with death. Prosthesis removal, which usually is necessary to treat these infections, produces large skeletal defects, shortening of the extremity, and severe functional impairment. The health cost of treating a single septic prosthetic joint has been conservatively at $50,000 to $60000, with an extrapolated expenditure of more than $200 million to $250 million per year in the United States alone. The patient faces protracted hospitalization, sizable financial expense, and potentially renewed disability (Mandell, Douglas and Bennett's: Principles and practice of infectious Disesases, Sixth ed., volume 2).

Prosthetic joints become infected by two different pathogenetic routes: locally introduced and hematogenous types of osteomyelitis. The locally introduced form of infection is the result of wound sepsis contiguous to the prosthesis or operative contamination. Any bacteremia can induce infection of a total joint replacement by the hematogenous route. Dentogingival infections and manipulations are known causes of Viridans streptococcal and anaerobic Peptostreptococcus infections in prosthesis. Pyogenic skins processes can cause staphylococcal and streptococcal (groups A, B, C and G streptococci) infections in joint replacements. Genitourinary and gastrointestinal tract procedures or infections are associated with gram-negative bacillary, Enterococci and anaeobic infections of prostheses. The frequency of the presence of the specific etiologic microorganisms in prosthetic joint sepsis varies among the published studies, but a general view of the spectrum of this bacteriology and the prominence of certain microbial groups is known. Staphylococci (coagulase-negative staphylococci and S. aureus) are the principal causative agents; aerobic streptococci and gram-negative bacilli are each responsible for 20% to 25%, and anaerobes represent 10% of these infections. The spectrum of microbial agents capable of causing prosthetic joint infection is unlimited and included organisms ordinarily considered "contaminants" of cultures, such as Bacillus spp. Although infections with fungi (particularly Candida) and mycobacteria are rare, these infections have been described (Mandell, Douglas and Bennett's: Principles and practice of infectious Diseases, Sixth ed., volume 2).

The gold standard for diagnosing prosthesis infection remains bacteriological analysis, which involved isolation and culture of the infecting bacteria at the site of infection, from relevant samples. Bacteriological analysis is generally considered as significant if at least 2 samples taken during the surgery are positive for streptococci, enterococci and Peptostreptococcus spp. Ultrasound-guided needle aspiration or image-guided core-needle biopsy can also be carried. Several drawbacks are however associated to bacteriological analysis. Conventional detection methods rely on the evidencing of Gram-positive bacteria on direct examination of the pathological specimen. However the microscopic detection of bacteria of the genus Streptococcus and related genera in clinical specimens has a limited sensitivity. It is therefore possible that a pathological specimen is not detected by direct microscopic examination of this pathological specimen. In addition, even though their structure is of Gram-positive bacteria type, they may give a false Gram-negative result after Gram staining of the pathological sample and give rise to erroneous or inconclusive identification. When a bacterium of one of the species of the genera under consideration is isolated in the laboratory, conventional phenotype identification methods are the most commonly used to identify bacteria of species belonging to genus Streptococcus and related genera, and several identification kits and automated analyzers have been developed to assist phenotype identification of bacteria of genus Streptococcus and related genera. In this respect, the extent of identification in routine practice is variable. In particular, one of the tests used for identifying streptococci and bacteria of related genera is the detection of a haemolytic reaction, i.e. the destruction by the bacterium of red blood cells contained in a blood agar. However, this haemolytic reaction can be inhibited by the presence of oxygen or by the presence of peroxide when streptococci bacteria are cultured in the presence of a high carbon dioxide concentration. Moreover, it is recognized that there exists a certain extent of subjectivity in assessing haemolysis by colonies of streptococci and hence inter-operator variability which is detrimental to the quality of identification of these.

There are currently no other methods for establishing the diagnosis of streptocococci, enterococci and Peptostreptotoccus spp. prosthesis infection. Thus the object of this invention proposes an alternative technique for the diagnosis of these infections. A serological approach based on the antibodies of anti-streptococci, anti-enterococci and anti-Peptostreptococcus spp. could overcome the drawbacks associated to bacteriological analysis.

SUMMARY OF THE INVENTION

The present invention arises from the unexpected identification, by the inventors, that the proteins 25D6, 25D3, 25H3, and 25C6 of S. agalactiae (represented respectively by SEQ ID NO: 2, SEQ ID NO: 4, SEQ ID NO: 6 and SEQ ID NO: 8) provide for efficient detection of anti-streptococci, anti-enterococci and anti-Peptostreptococcus spp. antibodies in biological samples.

Thus, the present invention relates to a method, in particular an in vitro method, for determining if an individual is infected by a bacterium selected from the group consisting Streptococcus, Enterococcus and Peptostreptococcus genera, preferably, a Streptococcus bacterium selected from the group consisting of beta-hemolytic Streptococcus and Viridans Streptococcus, or an Enterococcus bacterium selected from the group consisting of Enterococcus faecalis and Enterococcus faecium, or a Peptostreptococcus bacterium selected from the group consisting of Peptostreptococcus magnus, Peptostreptococcus asaccharolyticus, Peptostreptococcus anaerobius, Peptostreptococcus prevotii, and Peptostreptococcus micros comprising:

detection of antibodies directed against at least one protein of sequence SEQ ID NO: 2, SEQ ID NO: 4, SEQ ID NO: 6 or SEQ ID NO: 8, in a biological sample of the individual, and deduction therefrom that the individual is infected by a bacterium selected from the group consisting Streptococcus, Enterococcus and Peptostreptococcus genera, preferably a Streptococcus bacterium selected from the group consisting of beta-hemolytic Streptococcus and Viridans Streptococcus, or an Enterococcus bacterium selected from the group consisting of Enterococcus faecalis and Enterococcus faecium, or a Peptostreptococcus bacterium selected from the group consisting of Peptostreptococcus magnus, Peptostreptococcus asaccharolyticus, Peptostreptococcus anaerobius, Peptostreptococcus prevotii, and Peptostreptococcus micros.

According to said method, when antibodies directed against at least one protein of sequence SEQ ID NO: 2, SEQ ID NO: 4, SEQ ID NO: 6 or SEQ ID NO: 8 are detected in a biological sample of an individual, said individual is infected by a bacterium selected from the group consisting Streptococcus, Enterococcus and Peptostreptococcus genera. Inversely, if no antibody directed against at least one protein of sequence SEQ ID NO: 2, SEQ ID NO: 4, SEQ ID NO: 6 or SEQ ID NO: 8 is detected in a biological sample of an individual, said individual is not infected by a bacterium selected from the group consisting of Streptococcus, Enterococcus and Peptostreptococcus genera.

Accordingly detection of antibodies directed against a protein of sequence SEQ ID NO: 2 may be sufficient to deduce that an individual is infected by a bacterium selected from the group consisting Streptococcus, Enterococcus and Peptostreptococcus genera. Similarly, detection of antibodies directed against a protein of sequence SEQ ID NO: 4, or a sequence SEQ ID NO: 6 or a sequence SEQ ID NO: 8 may be sufficient to deduce that an individual is infected by a bacterium selected from the group consisting Streptococcus, Enterococcus and Peptostreptococcus genera. Typically, detection of antibodies directed against a protein of sequence SEQ ID NO: 2 and antibodies directed against a protein of sequence SEQ ID NO: 4 or detection of antibodies directed against a protein of sequence SEQ ID NO: 2 and antibodies directed against a protein of sequence SEQ ID NO: 6 or detection of antibodies directed against a protein of sequence SEQ ID NO: 2 and antibodies directed against a protein of sequence SEQ ID NO: 8, or detection of antibodies directed against a protein of sequence SEQ ID NO: 4 and antibodies directed against a protein of sequence SEQ ID NO: 6 or detection of antibodies directed against a protein of sequence SEQ ID NO: 4 and antibodies directed against a protein of sequence SEQ ID NO: 8 or detection of antibodies directed against a protein of sequence SEQ ID NO: 6 and antibodies directed against a protein of sequence SEQ ID NO: 8 may be sufficient to deduce that an individual is infected by a bacterium selected from the group consisting Streptococcus, Enterococcus and Peptostreptococcus genera. Similarly, detection of antibodies directed against a protein of sequence SEQ ID NO: 2 and of antibodies directed against a protein of sequence SEQ ID NO: 4 and of antibodies directed against a protein of sequence SEQ ID NO: 6 or detection of antibodies directed against a protein of sequence SEQ ID NO: 4 and of antibodies directed against a protein of sequence SEQ ID NO: 6 and of antibodies directed against a protein of sequence SEQ ID NO: 8, or detection of antibodies directed against a protein of sequence SEQ ID NO: 2 and of antibodies directed against a protein of sequence SEQ ID NO: 6 and of antibodies directed against a protein of sequence SEQ ID NO: 8, or detection of antibodies directed against a protein of sequence SEQ ID NO: 2 and of antibodies directed against a protein of sequence SEQ ID NO: 4 and of antibodies directed against a protein of sequence SEQ ID NO: 8 may be sufficient to deduce that an individual is infected by a bacterium selected from the group consisting Streptococcus, Enterococcus and Peptostreptococcus genera. Analogously; detection of antibodies directed against a protein of sequence SEQ ID NO: 2 and of antibodies directed against a protein of sequence SEQ ID NO: 4 and of antibodies directed against a protein of sequence SEQ ID NO: 6 and of antibodies directed against a protein of sequence SEQ ID NO: 8 may be sufficient to deduce that an individual is infected by a bacterium selected from the group consisting Streptococcus, Enterococcus and Peptostreptococcus genera.

Preferably, said detection of antibodies directed against at least one protein of sequence SEQ ID NO: 2, SEQ ID NO: 4, SEQ ID NO: 6 or SEQ ID NO: 8, in a biological sample of the individual comprises contacting the biological sample with:

(i) at least one protein of sequence SEQ ID NO: 2, SEQ ID NO: 4, SEQ ID NO: 6 or SEQ ID NO: 8; and/or, (ii) at least one homologous protein comprising or consisting of a sequence having at least 90% identity with a sequence SEQ ID NO: 2, SEQ ID NO: 4, SEQ ID NO: 6 or SEQ ID NO: 8; and/or, (iii) at least one fragment of protein defined in (i) or homologous protein defined in (ii);

provided the homologous protein defined in (ii) or the fragment defined in (iii) can be bound by at least one antibody directed against a protein of sequence SEQ ID NO: 2, SEQ ID NO: 4, SEQ ID NO: 6 or SEQ ID NO: 8.

Preferably said fragment defined in (iii) may comprise 4 to 200 contiguous amino acids of said proteins defined in (i) or of said homologous proteins defined in (ii).

As appropriate, a protein sequence comprising or consisting of a sequence SEQ ID NO: 2, or an homologous protein comprising or consisting of a sequence having at least 90% identity with a sequence SEQ ID NO: 2 or a fragment of said protein or said homologous protein may be used for detection of antibodies directed against protein of sequence SEQ ID NO: 2. Said method is applicable mutatis mutandis to SEQ ID NO: 4, SEQ ID NO: 6 and SEQ ID NO: 8.

Preferably, according to said method, the detection of antibodies directed against a protein of sequence SEQ ID NO: 2 is indicative of a patient having a bacterium from the Streptococcus genus or the Peptostreptococcus genus, more preferably, is indicative of a patient having a Peptostreptococcus bacterium selected from the group consisting of Peptostreptococcus magnus, Peptostreptococcus asaccharolyticus, Peptostreptococcus anaerobius, Peptostreptococcus prevotii, and Peptostreptococcus micros, or is indicative of a patient having a beta-hemolytic Streptococcus selected from the group consisting of Streptococcus pyogenes, Streptococcus agalactiae, Streptococcus alactolyticus, Streptococcus equisimilis and Streptococcus dysgalactiae.

Preferably, according to said method, the detection of antibodies directed against a protein of sequence SEQ ID NO: 8 is indicative of a patient having a bacterium from the Streptococcus genus or the Enterococcus genus, more preferably, is indicative of a patient having a Enterococcus faecalis bacterium or is indicative of a patient having a Streptococcus bacterium such as a beta-hemolytic Streptococcus selected from the group consisting of Streptococcus pyogenes, Streptococcus agalactiae, Streptococcus equisimilis and Streptococcus dysgalactiae or is indicative of a patient having a Streptococcus bacterium such as a Viridans streptococcus bacterium selected from the group consisting of Streptococcus mitis, Streptococcus oralis, Streptococcus sanguis, Streptococcus parasanguis and Streptococcus gordonii.

The present invention also relates to the use of:

(i) at least one protein of sequence SEQ ID NO: 2, SEQ ID NO: 4, SEQ ID NO: 6 or SEQ ID NO: 8; or (ii) at least one homologous protein comprising or consisting of a sequence having at least 90% identity with a sequence SEQ ID NO: 2, SEQ ID NO: 4, SEQ ID NO: 6 or SEQ ID NO: 8; or (iii) at least one fragment of protein defined in (i) or homologous protein defined in (ii), provided the homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8, for in vitro diagnosis of infection with a bacterium selected from the group consisting of Streptococcus, Enterococcus and Peptostreptococcus genera.

Preferably said fragment defined in (iii) may comprise 4 to 200 contiguous amino acids of said proteins defined in (i) or of said homologous proteins defined in (ii).

The present invention also relates to a kit for diagnosing an infection by a bacterium selected from the group consisting of Streptococcus, Enterococcus and Peptostreptococcus genera comprising antigens which can be bound by antibodies directed against at least two sequences selected from the group consisting of SEQ ID NO: 2, SEQ ID NO: 4, SEQ ID NO: 6 and SEQ ID NO: 8, wherein said antigens are:

(i) at least one protein of sequence SEQ ID NO: 2, SEQ ID NO: 4, SEQ ID NO: 6 or SEQ ID NO: 8; or, (ii) at least one homologous protein comprising or consisting of a sequence having at least 90% identity with a sequence SEQ ID NO: 2, SEQ ID NO: 4, SEQ ID NO: 6 or SEQ ID NO: 8; or, (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 2, SEQ ID NO: 4, SEQ ID NO: 6 and SEQ ID NO: 8.

Preferably said fragment defined in (iii) may comprise 4 to 200 contiguous amino acids of said proteins defined in (i) or of said homologous proteins defined in (ii).

The present invention also related to an in vitro method, for determining if an individual is infected by a bacterium selected from the group consisting Streptococcus, Enterococcus and Peptostreptococcus genera, preferably, a Streptococ-

*cus* bacterium selected from the group consisting of beta-hemolytic *Streptococcus* and Viridans *Streptococcus*, or an *Enterococcus* bacterium selected from the group consisting of *Enterococcus faecalis* and *Enterococcus faecium*, or a *Peptostreptococcus* bacterium selected from the group consisting of *Peptostreptococcus magnus, Peptostreptococcus asaccharolyticus, Peptostreptococcus anaerobius, Peptostreptococcus prevotii*, and *Peptostreptococcus micros* comprising:

contacting capture ligands specific of at least one protein of sequence SEQ ID NO: 2, SEQ ID NO: 4, SEQ ID NO: 6 or SEQ ID NO: 8, with a biological sample of the individual;

determining if said protein is bound to the specific capture ligands;

deducing therefrom that the individual is infected by a bacterium selected from the group consisting *Streptococcus, Enterococcus* and *Peptostreptococcus* genera, preferably, a *Streptococcus* bacterium selected from the group consisting of beta-hemolytic *Streptococcus* and Viridans *Streptococcus*, or an *Enterococcus* bacterium selected from the group consisting of *Enterococcus faecalis* and *Enterococcus faecium*, or a *Peptostreptococcus* bacterium selected from the group consisting of *Peptostreptococcus magnus, Peptostreptococcus asaccharolyticus, Peptostreptococcus anaerobius, Peptostreptococcus prevotii*, and *Peptostreptococcus micros*.

In an embodiment of the invention, the above-defined method comprises contacting specific capture ligands of at least two proteins of sequence SEQ ID NO: 2, SEQ ID NO: 4, SEQ ID NO: 6 or SEQ ID NO: 8.

The present invention also relates to the use, in particular the in vitro use, of specific capture ligands, in particular an antibody, directed against a protein of sequence SEQ ID NO: 2, SEQ ID NO: 4, SEQ ID NO: 6 or SEQ ID NO: 8 for determining if an individual is infected by a bacterium selected from the group consisting *Streptococcus, Enterococcus* and *Peptostreptococcus* genera, preferably, a *Streptococcus* bacterium selected from the group consisting of beta-hemolytic *Streptococcus* and Viridans *Streptococcus*, or an *Enterococcus* bacterium selected from the group consisting of *Enterococcus faecalis* and *Enterococcus faecium*, or a *Peptostreptococcus* bacterium selected from the group consisting of *Peptostreptococcus magnus, Peptostreptococcus asaccharolyticus, Peptostreptococcus anaerobius, Peptostreptococcus prevotii*, and *Peptostreptococcus micros*. In other words, the present invention also relates to a method for the in vitro diagnosis of an infection by a bacterium selected from the group consisting of *Streptococcus, Enterococcus* and *Peptostreptococcus* genera, preferably, a *Streptococcus* bacterium selected from the group consisting of beta-hemolytic *Streptococcus* and Viridans *Streptococcus*, or an *Enterococcus* bacterium selected from the group consisting of *Enterococcus faecalis* and *Enterococcus faecium*, or a *Peptostreptococcus* bacterium selected from the group consisting of *Peptostreptococcus magnus, Peptostreptococcus asaccharolyticus, Peptostreptococcus anaerobius, Peptostreptococcus prevotii*, and *Peptostreptococcus micros*. in an individual, in whom one detects the presence of at least an antigen of the aforesaid bacterium in a biological sample of the individual using a ligand of capture, in particular an antibody, directed against a protein of sequence SEQ ID NO: 2, SEQ ID NO: 4, SEQ ID NO: 6 or SEQ ID NO: 8.

The present invention also relates to an antigenic kit for diagnosing an infection by a bacterium selected from the group consisting of *Streptococcus, Enterococcus* and *Peptostreptococcus* genera, preferably, selected from the group consisting of beta-hemolytic *Streptococcus, Viridans Streptococcus, Enterococcus* and *Peptostreptococcus* spp., comprising a capture ligand, in particular an antibody, directed against a protein of sequence SEQ ID NO: 2, SEQ ID NO: 4, SEQ ID NO: 6 or SEQ ID NO: 8.

DETAILED DESCRIPTION OF THE INVENTION

As intended herein, the expressions "*Streptococcus*", "Streptococci", or "Streptococcal" relates to a bacterium or to bacteria of the *Streptococcus* genus. The *Streptococcus* genus is composed of (i) the alpha-hemolytic group composed by the Viridans group and the pneumococci, (ii) the beta-hemolytic group composed of 18 antigenic groups classified between A to H and K to L (iii) the non hemolytic group also known as Enterococci. This last group has been re-classified en 1984 and defines currently the *Enterococcus* genus.

Preferably, the beta-hemolytic streptococci of the invention may be a *Streptococcus pyogenes* (also known as group A *Streptococcus* GAS), *Streptococcus agalactiae* (also known as group B *Streptococcus* GBS), *Streptococcus alactolyticus* (also known as group G *Streptococcus* GGS) and *Streptococcus dysgalactiae* (also known as group C *Streptococcus* GCS).

Preferably, the alpha-hemolytic streptococci of the invention may be a Viridans *streptococcus* more preferably said Viridans *streptococcus* bacterium may be selected from the group consisting of *Streptococcus mitis, Streptococcus oralis, Streptococcus sanguis, Streptococcus parasanguis* and *Streptococcus gordonii*.

As intended herein, the expressions "*Peptostreptococcus*", "Peptostreptococci", or "Peptostreptococcal" relates to a bacterium or to bacteria of the *Peptostreptococcus* genus. Preferably, the *Peptostreptococcus* may be *Peptostreptococcus magnus, Peptostreptococcus asaccharolyticus, Peptostreptococcus anaerobius, Peptostreptococcus* prevotii, and *Peptostreptococcus micros*.

As intended herein, the expressions "*enterococcus*", "enterocci", or "enteroccal" relates to a bacterium or to bacteria of the enteroccus genus. The enterocci of the invention may be an *Enterococcus faecalis*, or an *Enterococcus faecium*.

As intended herein, the expression 'infected' or 'infection' relates to individuals carrying bacteria selected from the group consisting of *Streptococcus, Enterococcus* and *Peptostreptococcus* genera as defined above. Preferably, the infection is a surface associated infection or a biofilm-associated infection. Infections by *Streptococcus, Enterococcus* or *Peptostreptococcus* genera can occur by bacterial biofilms. Preferably, the infected individuals present one or more sites wherein multiplication of the bacteria is occurring. Infections by a bacterium selected from the group consisting of *Streptococcus, Enterococcus* and *Peptostreptococcus* genera can occur as a consequence of the contact of internal tissues with a foreign material contaminated by a bacterium selected from the group consisting of *Streptococcus, Enterococcus* and *Peptostreptococcus* genera, in particular in a hospital setting. Accordingly, as intended herein, the infection preferably arises from the implantation of a prosthetic material in the individual, such as prosthetic joint, notably selected from the group consisting of a knee joint, a shoulder joint and a hip joint. Thus, the infection may be a device-associated-infection. Said device may be a medical device implanted in an individual such as prosthesis. Indeed, the infection may be a prosthetic or a periprosthetic infection and notably a periprosthetic joint infection.

Accordingly, as intended herein, the method according to the invention is implemented in order to determine if an individual suffers from an infection by a bacterium selected from the group consisting of *Streptococcus, Enterococcus* and *Peptostreptococcus* genera, the mentioned infection being selected among an infection on prosthesis (in particular articular) such as a periprosthetic joint infection, an osteoarticular infection, a post-operative infection (in particular during the installation of a foreign material such as a prosthesis), a dental infection, a parodontite, a conjunctivitis, a endophtalmy, a cerebral abscess, a empyeme under-dural, a lung infection, a peritonitis, an osteomyelitis, a septic arthritis, an endocarditis (in particular on prosthesis), a meningitis (in particular on shunts).

The individual can moreover be an individual diabetic, presenting an immunodepression, suffering of a cancer and/or carrying prosthetic material or catheter. Preferably the individual presenting a prosthetic joint selected from the group consisting of a knee joint, a shoulder joint and a hip joint. According to the invention, such a prosthetic joint may be infected by said a bacterium selected from the group consisting of *Streptococcus, Enterococcus* and *Peptostreptococcus* genera. As intended herein, the expression 'biological sample' includes both the sample as taken and the sample which has been subjected to various treatments, in particular to render it suitable for the use in the processes and methods according to the invention. The 'biological sample' according to the invention can be of any type liable to harbor antibodies, however, it is preferred that the biological sample is selected from the group consisting of a blood sample, a serum sample, a plasma sample, a mucosa-associated lymphoid tissue (MALT) sample, a cerebrospinal fluid sample, an articular liquid sample, a pleural liquid sample, a saliva sample, and an urine sample.

As intended herein, the expression 'determining if an individual is infected by a bacterium selected from the group consisting *Streptococcus, Enterococcus* and *Peptostreptococcus* genera' encompasses establishing a diagnosis or diagnosing an infection by a bacterium selected from the group consisting of *Streptococcus, Enterococcus* and *Peptostreptococcus* genera in an individual. It also encompasses following-up of individuals having undergone a surgical operation for implanting, cleaning or replacing the prosthesis. It further encompasses following the evolution of infection by a bacterium selected from the group consisting of *Streptococcus, Enterococcus* and *Peptostreptococcus* genera, in particular within the framework of a therapeutic treatment. Accordingly, it is preferred that the individual is under treatment by antibiotics.

Determining if antibodies directed against a protein of sequence SEQ ID NO: 2, SEQ ID NO: 4, SEQ ID NO:6 and SEQ ID NO: 8, are present in a biological sample of the individual can be carried out by various methods well known to one of skill in the art. However, determining if antibodies directed against a protein comprising or consisting of a sequence selected from the group consisting of SEQ ID NO:2, 4, 6 or 8, are present in a biological sample of the individual comprises:

contacting the biological sample with:
(i) a protein of sequence SEQ ID NO: 2, SEQ ID NO: 4, SEQ ID NO: 6 or SEQ ID NO: 8; or
(i) a homologous protein of sequence having at least 90% identity with a sequence SEQ ID NO: 2, SEQ ID NO: 4, SEQ ID NO: 6 or SEQ ID NO: 8; or
(iii) at least one fragment of said protein of sequence SEQ ID NO: 2, SEQ ID NO: 4, SEQ ID NO: 6 or SEQ ID NO: 8 or of said homologous protein;

provided said homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8;

detecting antibodies, preferably IgG, bound to said protein of sequence SEQ ID NO: 2, SEQ ID NO: 4, SEQ ID NO: 6 or SEQ ID NO: 8, to said homologous protein or to said at least one fragment.

Preferably said fragment defined in (iii) may comprise 4 to 200 contiguous amino acids of said proteins defined in (i) or of said homologous proteins defined in (ii).

The protein of sequence SEQ ID NO: 2, SEQ ID NO: 4, SEQ ID NO: 6 or SEQ ID NO: 8; the homologous protein thereto, or the fragments thereof, can present either as polypeptide chains resulting from the in vivo, ex vivo or in vitro polymerization of amino acids selected from the 20 natural amino acids, or as modified polypeptide chains. As intended herein, in vivo or ex vivo polymerization notably encompasses production by in vitro translation or by chemical synthesis. Where the polypeptide is modified, it can result from the use of non-natural amino acids during the in vivo, ex vivo or in vitro polymerization of the polypeptide chain and from post-polymerisation modifications. The polypeptide can be modified one or several times by identical or different modifications. The modifications can be anywhere in the polypeptide chain, and notably in the peptide backbone, in the amino acid lateral groups, or at the N-terminal or C-terminal extremities of the polypeptide chain. Modification notably encompass acylation, in particular acetylation, palmytoylation, glypiation, prenylation and myristoylation, ADP-ribosylation, amidation, covalant linkage of a lipid, such as phosphatidylinositol, flavin, an heme, or a nucleotide, covalent, or non-covalent cross-linking, cyclisation, disulfide bridge oxidation and reduction, methylation and demethylation, pyroglutamate formation, formylation, gamma-carboxylation, glycosylation, hydroxylation, iodation, phosphorylation, selenoylation, sulfatation, racemisation, addition of aminoacids, such as arginylation, or of polypeptides, such as ubiquitinylation (Proteins structure and molecular properties, 2nd ed., T. E. Creighton, W. H. Freeman and Company, New York (1993) and Wold, F., Posttranslational Protein Modifications: Prospects and Prospective customers, pgs 1-12 in Covalent posttranslational modification of proteins, B. C. Johnson, ED., Press Academy, New York (1983); Seifter et al. (1990) Meth. Enzymol. 182: 626-646 and Rattan et al. (1992) Protein Synthesis: Posttranslational Modifications and Aging, Ann. NR. Y. Acad. Sci. 663: 48-62).

Besides, where they are obtained by recombining means, the polypeptide chain or the protein of sequence SEQ ID NO: 2, SEQ ID NO: 4, SEQ ID NO: 6 or SEQ ID NO: 8, the homologous protein thereto, and the fragments thereof, may also comprise sequences useful for protein purification (so-called purification tags), such as polyhistidine tags, and optionally a sequence enabling the cleavage of these tags, such as protease cleavage sites.

Preferably, the protein of sequence SEQ ID NO: 2, SEQ ID NO: 4, SEQ ID NO: 6 or SEQ ID NO: 8 may comprise 350, 400, 500, or 1000 amino-acids at the most. More preferably the proteins of SEQ ID NO: 2, SEQ ID NO: 4, SEQ ID NO: 6 or SEQ ID NO: 8, respectively consist in SEQ ID NO: 2 or SEQ ID NO: 17, SEQ ID NO: 4 or SEQ ID NO: 18, SEQ ID NO: 6 or SEQ ID NO: 19, and SEQ ID NO: 8 or SEQ ID NO: 20. Preferably proteins of sequences SEQ ID NO: 2, SEQ ID NO: 4, SEQ ID NO: 6, and SEQ ID NO: 8 are respectively encoded by nucleic acids comprising or consisting of SEQ ID NO: 1, SEQ ID NO: 3, SEQ ID NO: 5, and SEQ ID NO: 7.

The percentage of identity according to the invention can be calculated by methods well-known to one of skill in the art. The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

The term "homologous protein" or "homologous polypeptide" means a protein having a percentage of identity with proteins of SEQ ID NO: 2, SEQ ID NO: 4, SEQ ID NO: 6 or SEQ ID NO: 8 according to the invention.

Preferably, the percentage of identity relates to the number of identical amino-acids obtained for an optimal paired alignment (i.e. the alignment maximizing the number of identical amino-acids) of the sequence of a protein homologous to SEQ ID NO: 2, SEQ ID NO: 4, SEQ ID NO: 6 or SEQ ID NO: 8, divided by the total number of amino-acids in SEQ ID NO: 2, 4, 6 or 8. Alignment can be performed manually or using computer programs such as the EMBOSS-Needle program (Needleman and Wunsch (1970) J. Mol. Biol. 48:443-453). Preferably, the percentage of identity according to the invention is at least 85%, more preferably from at least 90%, and even more preferably from at least 95%. Preferably, the fragment contains an epitope. The smaller fragment that may be recognized by an antibody may have 4 to 5 contiguous amino acids. Consequently, according to the invention a 'fragment' may be of 4, 5, 6, 7, 8, 9, 10, 11, 12, 13, 14, 15, 16, 17, 18, 19, 20 contiguous amino acids. Preferably, said fragment may comprise 22 to 200 contiguous amino acids, more preferably 25 to 150 contiguous amino acids, and more preferably 30 to 100 contiguous amino acids. Preferably also, the 'fragment' may comprise 35 to 80 contiguous amino acids, more preferably 40 to 75 contiguous amino acids at the most, and most preferably 45 to 70 contiguous amino acids at the most. Preferably also, the 'fragment' according to the invention consists of a portion of a sequence SEQ ID NO: 2, SEQ ID NO: 4, SEQ ID NO: 6 or SEQ ID NO: 8, or of a portion of sequences presenting at least 85%, more preferably at least 90%, and more preferably from at least 95% of a sequence SEQ ID NO: 2, SEQ ID NO: 4, SEQ ID NO: 6 or SEQ ID NO: 8 at the most.

As intended herein, the homologous protein as defined above and the at least one fragment as defined above can be bound by at least one antibody directed against a protein of sequence SEQ ID NO: 2, SEQ ID NO: 4, SEQ ID NO: 6 or SEQ ID NO: 8. In other words, the homologous protein as defined above and the at least one fragment as defined above comprises at least one of the epitopes of a protein of sequence SEQ ID NO: 2, SEQ ID NO: 4, SEQ ID NO: 6 or SEQ ID NO: 8. Accordingly, the homologous protein as defined above and the at least one fragment as defined above comprise at least one of the epitopes of a protein of sequence SEQ ID NO: 2, SEQ ID NO: 4, SEQ ID NO: 6 or SEQ ID NO: 8. Accordingly, the homologous protein as defined above and the at least one fragment as defined above should preferably be such that they provide at least 70%, more preferably at least 80% and most preferably at least 90%, of the sensitivity provided by the protein of sequence SEQ ID NO: 2, SEQ ID NO: 4, SEQ ID NO: 6 or SEQ ID NO: 8, measured in the same conditions.

As intended herein, the term 'sensitivity' is defined as the percentage of individuals infected by a bacterium selected from the group consisting of *Streptococcus, Enterococcus* and *Peptostreptococcus* genera, which biological samples, such as serum samples, are determined to contain antibodies directed against a protein of sequence SEQ ID NO: 2, SEQ ID NO: 4, SEQ ID NO: 6 or SEQ ID NO: 8, detectable according to the invention. The determining of the sensitivity provided by an antigen can be carried out according to various methods well-known to one of skill in the art and notably as illustrated in the following Example 1. Preferably, the antibodies detected in the biological samples according to the invention are IgG.

In addition, as that will appear clearly to one of skill in the art, 'an antibody directed against at least one protein of sequence SEQ ID NO: 2, SEQ ID NO: 4, SEQ ID NO: 6 or SEQ ID NO: 8' means any antibody of the individual able to recognize a protein of a sequence SEQ ID NO: 2, SEQ ID NO: 4, SEQ ID NO: 6 or SEQ ID NO: 8, i.e. a specific antibody of this protein, but which can also recognize:

a larger protein of sequence SEQ ID NO: 2, SEQ ID NO: 4, SEQ ID NO: 6 or SEQ ID NO: 8; or a homologous protein comprising or consisting of a sequence having at least 90% identity with a sequence SEQ ID NO: 2, SEQ ID NO: 4, SEQ ID NO: 6 or SEQ ID NO: 8;

a fragment of homologous protein or a protein of sequence SEQ ID NO: 2, SEQ ID NO: 4, SEQ ID NO: 6 or SEQ ID NO: 8. Preferably said fragment defined in (iii) may comprise 4 to 200 contiguous amino acids of said proteins defined in (i) and/or of said homologous proteins defined in (ii).

Providing the detection of antibodies directed against a protein of sequence SEQ ID NO: 2, SEQ ID NO: 4, SEQ ID NO: 6 or SEQ ID NO: 8, in the biological samples, or the antigen detection of a bacterium selected from the group consisting of *Streptococcus, Enterococcus* and *Peptostreptococcus* genera, preferably selected from the group consisting of beta-hemolytic *Streptococcus, Viridans Streptococcus, Enterococcus* and *Peptostreptococcus* spp. using a ligand of capture, such as an antibody, directed, preferably specifically, against a protein of sequence SEQ ID NO: 2, SEQ ID NO: 4, SEQ ID NO: 6 or SEQ ID NO: 8, can be easily implemented by one of skill in the art.

Being the detection of antibody directed against a protein of sequence SEQ ID NO: 2, SEQ ID NO: 4, SEQ ID NO: 6 or SEQ ID NO: 8, in the biological samples, it can be carried out with the assistance (i) of at least one protein of sequence SEQ ID NO: 2, SEQ ID NO: 4, SEQ ID NO: 6 or SEQ ID NO: 8; or (ii) of at least one homologous protein comprising or consisting of a sequence dividing at least 90% identity with a sequence SEQ ID NO: 2, SEQ ID NO: 4, SEQ ID NO: 6 or SEQ ID NO: 8; or (iii) of at least one fragment of protein defined in (i) or homologous protein defined in (ii), the fragment comprising 4 to 200 contiguous amino acids of said protein defined in (i) or homologous protein defined in (ii).

Preferably said fragments defined in (iii) may comprise 4 to 200 contiguous amino acids of said proteins defined in (i) or of said homologous proteins defined in (ii).

Preferably, in the above-defined method, detecting antibodies can be carried out with specific detecting ligands of the antibodies.

As intended herein, a "ligand" is a compound liable to specifically bind to a target, such as an antibody or an antigen. The ligand can be of any type but preferably, it is an antibody, an aptamer, or a peptide obtained by phage display. To determine whether antibodies or antigens are fixed by a ligand of capture one can use a ligand detection, which can be specific either antibodies or antigens fixed, or of the ligands of capture.

The methods calling upon ligands of capture and ligands of detection are well-known to one of skill of the art, and can be performed according to various well-known formats, solid or homogeneous phase, one or two stages, using a method sandwich or by competition. Preferably, the ligand of capture is immobilized on a solid phase, such as the walls of a well of a plate of microtitration or paramagnetic balls.

As intended herein, an "antigen" relates to any substance that triggers the production of an antibody by the immune system in an animal, including a human. Antigen refers also to a substance which is a ligand of an antibody to which it binds. The term "epitope" as used herein means the portion of the antigen which interacts with an antibody. When the antigen is a protein, said portion may be a specific amino acid sequence, a modified amino acid sequence, or a protein secondary or tertiary structure.

An "antibody" as intended herein relates to antibodies belonging to any species, such as human, mouse, rat, rabbit, goat, or camelidae species. The antibody can also be a chimeric antibody, i.e. an antibody which comprises parts originating from different species. Preferred chimeric antibodies are so-called "humanized" antibodies, wherein the constant parts (CH and CL) are of human origin and the variable parts (VH and VL) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')2, scFv fragments as well as camelidae single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) Nature 346:818-822 and Bock et al. (1992) Nature 355:564-566. The aptamers of a peptide nature and the production thereof are described, in particular, by Hoppe-Seyler et al. (2000) J. Mol. Med. 78:426-430.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott and Smith (1990) Science 249:386-390, and Marks et al. (1991) J. Mol. Biol. 222:581-597. Preferably, the polypeptide obtainable by phage display is an scFv-type polypeptide (single-chain variable fragment). This technique is described, in particular, by Winter et al. (1994) Annu. Rev. Immunol. 12:433-455.

The term "specific", when it refers to recognition of a ligand or binding of a ligand to a first target, such as an antigen or an antibody, means that the ligand interacts with the first target without interacting substantially with another target which does not structurally resemble the first target, for example, the ligand. Preferably the antibody directed against a polypeptide of sequence SEQ ID NO: 2, SEQ ID NO: 4, SEQ ID NO: 6 or SEQ ID NO: 8 does not bind to a polypeptide having less than 85%, preferably 90%, sequence identity with SEQ ID NO: 2, SEQ ID NO: 4, SEQ ID NO: 6 or SEQ ID NO: 8, as appropriate.

As defined herein, the term "binds specifically" or similar terms, when used in the context of an antibody binding a target epitope, refers to the antibody having specificity for the target epitope (as opposed to other epitopes). The specificity need not be 100%. In one embodiment, the specificity is about 75% or greater (i.e., 75% specificity for the epitope). This means that about 75% of the antibodies that bind to an epitope will bind to the target epitope and about 25% of the antibodies will bind non-specifically. In another embodiment, the specificity is about 90% or greater.

In the above-defined method, determining if the capture ligands are respectively bound to an antigen can be carried out by using a detection ligand which is specific of said antigen but preferably binds to said antigen by recognition of an another binding site (i.e. epitope) than the recognition site of said capture ligand.

Preferably, the "detection ligand" according to the invention means marking or labeling molecules for detecting the ligand. The term 'marking' or "labeling" refers both to a direct labelling and to an indirect labelling (for example, by means of other ligands, themselves directly labelled, or using reagents of a labelled "affinity pair", such as, but not exclusively, the labelled avidin-biotin pair, etc.). Preferably, the label is a radioisotope, an enzyme or a fluorophore.

As will be clear to one of skill in the art, in the above-defined method, the protein of sequence SEQ ID NO: 2, SEQ ID NO: 4, SEQ ID NO: 6 or SEQ ID NO: 8, the homologous protein or the fragment can be used as a capture antigen.

Methods using capture antigens or ligands and detection ligands are well known to one of skill in the art and can be carried out in accordance with various well-known formats, for example in solid or homogeneous phase, in one or two steps, by a sandwich method or by a competitive method.

Preferably, the capture antigen or ligand is immobilised on a solid phase. By way of non-limiting examples of solid phase, microplates could be used, in particular polystyrene microplates, solid optionally paramagnetic particles or beads, or even polystyrene or polypropylene test tubes, glass, plastic or silicon chips, etc.

Although having distinct significances, the terms comprising, 'containing', and 'consisting of' were used in an interchangeable way in the description of the invention, and can be replaced one by the other.

The invention will be further described in view of the following examples.

Summary of the sequences described herein:

| Sequence description | SEQ ID NO: |
| --- | --- |
| 25D6 nucleotide sequence | 1 |
| 25D6 protein sequence | 2 |
| 25D3 nucleotide sequence | 3 |
| 25D3 protein sequence | 4 |
| 25H3 nucleotide sequence | 5 |
| 25H3 protein sequence | 6 |
| 25C6 nucleotide sequence | 7 |
| 25C6 protein sequence | 8 |
| 25E1 nucleotide sequence | 9 |
| 25E1 protein sequence | 10 |
| 26D3 nucleotide sequence | 11 |
| 26D3 protein sequence | 12 |
| 26E3 nucleotide sequence | 13 |
| 26E3 protein sequence | 14 |
| 25E3 nucleotide sequence | 15 |
| 25E3 protein sequence | 16 |
| 25D6 + His tag protein sequence | 17 |
| 25D3 + His tag protein sequence | 18 |
| 25H3 + His tag protein sequence | 19 |
| 25C6 + His tag protein sequence | 20 |
| 25E1 + His tag protein sequence | 21 |
| 26D3 + His tag protein sequence | 22 |
| 26E3 + His tag protein sequence | 23 |
| 25E3 + His tag protein sequence | 24 |

EXAMPLES

Example 1

Materials and Methods

Antigens 25D6 (SEQ ID NO: 17), 25D3 (SEQ ID NO: 18), 25H3 (SEQ ID NO: 19), 25C6 (SEQ ID NO: 20), 25E1 (SEQ ID NO: 21), 26D3 (SEQ ID NO: 22), 26E3 (SEQ ID NO: 23) and 25E3 (SEQ ID NO: 24) were recombinantly produced in *Escherichia coli* and purified according to usual methods, such as described in Lavallie (1995) "Production of recombinant proteins in *Escherichia coli*". Unit 5.1. Current Protocols in Protein Science; Scopes (1995) "Strategies for protein purification" Unit 1.2. Current Protocols in Protein Science.

First screening was performed by high throughput ELISA. ELISA plates were coated overnight with 0,5 µg/mL of purified antigens (proteins 25D6, 25D3, 25H3, 25C6, 25E1, 26D3, 26E3, 25E3). The plates were further saturated 2 hours with PBS-TWEEN containing 4% serum albumin bovine (SAB). Hundred microliters of each serum sample of patients or controls were added at a 1/100 dilution for 30 minutes. Human peroxydase-labeled anti-IgG antibody was then added for 30 minutes before revelation with tetrabenzimidine (TMB) for approximately 15 minutes. Sulphuric acid (100 µL) were then added in each well to stop the reaction. The 450 nm absorbance of each well was then measured after 5 minutes. Are regarded as 'positive' in ELISA, the serums identified by their binding to polypeptides (antigens) such as defined according to the invention.

Pertinent antigens were then tested with sensitive technology LUMINEX®. Briefly, the antigens were covalently attached to surface carboxyl groups of MAGPLEX MICROSPHERES (LUMINEX®) using N-hydroxysulfosuccinimide (sulfo-NHS) and 1-ethyl-3-(3-dimethylaminopropyl) carbodiimide hydrochloride (EDC) according the manufacturer's instructions. 50 µg were used for attachment to 5.000,000 microspheres. Detection of serum antibodies was carried out according to the manufacturer's instructions. Briefly, antigen-coupled microspheres were added to the wells of a multiwell plate and contacted with the various sera for a time sufficient to allow antibody-antigen complexes to be formed. After discarding the unreacted serum and washing the plate, a phycoerythrin-labeled anti-IgG antibody was added to the microspheres. Antibody-antigen complexes were further revealed by determining the mean fluorescence intensity (MFI) for each serum with a LUMINEX® analyzer.

The cut-off values for each serologic assay were determined by Receiver Operating Characteristics (ROC) curve analysis as described in the guideline GP10-A of December 1995 from the National Committee for Clinical Laboratory Standards (NCCLS) as the values yielding a maximum efficiency. The efficiency is defined as the ratio of the sum of the true positive samples and the true negative samples obtained with the serologic assays by the total number of samples assayed. True positive and negative samples are samples which are respectively determined as being positive and negative both using the serologic assay of the invention and bacteriological analysis. A sample was then considered positive if the antibody titer exceeded the defined cut-off value.

Example 2

Use of polypeptides of the invention for the detection of antibody in serum samples: first screening by high throughput ELISA.

The panel of samples tested is consisting of serum samples of 26 patients suffering from prosthetic joint infections wherein the infection with Viridans and beta hemolytic streptococci (A, B, C and G groups), *Peptostreptococcus* spp. was diagnosed positive with culture of 2 or more samplings on the infected prostheses. Control sera were collected from 64 healthy blood donors.

TABLE 1

Results (ELISA) obtained by testing of the antigens

| Ratio of positive sera | Tested antigens | | | | | | | |
|---|---|---|---|---|---|---|---|---|
| | 25D6 | 25D3 | 25H3 | 25C6 | 25E1 | 26D3 | 26E3 | 25E3 |
| Positive patients (26) | 44% | 50% | 31% | 46% | 7% | 19% | 11% | 7% |
| Healthy blood donors (64) | 11% | 11% | 11% | 11% | 9% | 12% | 9% | 8% |

Table 1 shows the results obtained according to the invention for polypeptides 25D6 (SEQ ID NO: 17), 25D3 (SEQ ID NO: 18), 25H3 (SEQ ID NO: 19), 25C6 (SEQ ID NO: 20), 25E1 (SEQ ID NO: 21), 26D3 (SEQ ID NO: 22), 26E3 (SEQ ID NO: 23), and 25E3 (SEQ ID NO: 24), with secondary antibodies recognizing the immunoglobulins G present in serum samples of patients or control healthy blood donors.

Results show that polypeptides of the invention 25D6 (SEQ ID NO: 17), 25D3 (SEQ ID NO: 18), 25H3 (SEQ ID NO: 19), and 25C6 (SEQ ID NO: 20) can be used for the diagnosis of infections of β hemolytic and *Viridans streptococci, Peptostreptococcus* spp. on articular prostheses. Other polypeptides also tested, such as 25E1 (SEQ ID NO: 21), 26D3 (SEQ ID NO: 22), 26E3 (SEQ ID NO: 23), and 25E3 (SEQ ID NO: 24) do not allow the diagnosis of such infections with no sufficient sensitivity.

Example 3

Use of polypeptides of the invention for the diagnosis of the beta hemolytic and Viridans streptococci, enterococci and *Peptostreptococcus* spp. prosthesis infections with panels of patient serum samples and control serum samples: evaluation by the LUMINEX® technology of the selected antigens.

The panel of samples tested is consisting of serum samples of 16 patients suffering from prosthetic joint infections wherein the infection with beta hemolytic streptococci (A, B, C, G groups) was diagnosed positive with culture of 2 or more samplings on the infected prostheses. Moreover, serums samples from 4 patients positive for a prosthesis infection to Viridans streptococci (3 *S. mitis*, 1 *S. oralis*), serum samples from 2 patients positive for a prosthesis infection to *Peptostreptococcus* spp., and serum samples from 3 patients positive for a prosthesis infection to *Enterococcus faecalis*, diagnosed positive with culture were tested. Control sera were collected from (i) 34 healthy prosthesis carriers with no clinical sign of infection since at least 2 years and (ii) 31 patients with prosthesis infections other than streptococci, enterococci, or *Peptostreptococcus* spp. infections; i.e. gram-positive coccus (n=1), *Corynebacterium* spp. (n=1), *Enterobacter aerogenes* (n=1), *Enterobacter cloacae* (n=2), *Escherichia coli* (n=1), *Klebsiella oxytoca* (n=1), *Propionibacterium acnes* (n=5), *Pseudomonas aeruginosa* (n=1), *Propionibacterium granulosum* (n=1), *Pasteurella multocida* (n=1), *Propionibacterium avidum* (n=1), *Staphylococcus aureus* (n=7), *Staphylococcus capitis* (n=4), coagulase negative staphylococci (n=2), *Serratia marcescens* (n=1), *Staphylococcus warneri* (n=1).

TABLE 2

Results (LUMINEX ® technology) obtained
by testing of the selected antigens.

| | Tested antigens | | | |
|---|---|---|---|---|
| Ratio of positive sera | 25D6 | 25D3 | 25H3 | 25C6 |
| Beta hemolytic *streptococci* positive patients (16) | 73% | 87% | 80% | 73% |
| Viridans *streptococci* positive patients (4) | 50% | 50% | 50% | 50% |
| *Peptostreptococcus* spp. positive patients (2) | 100% | 50% | 50% | 0% |
| *Enterococcus faecalis* positive patients (3) | 0% | 33% | 33% | 33% |
| Healthy prosthesis carriers (22) | 14% | 5% | 9% | 0% |
| Infected prosthesis patients with other infections than *streptococci*, *Enterococci*, or *Peptostreptococcus* spp . . . (31) | 23% | 19% | 26% | 16% |

The results show a significant antibody response (the probability associated with a test of X2 is lower than 0.05) against the polypeptides identified according to the invention during the infections to β hemolytic *streptococci*, *Viridans streptococci*, *Peptostreptoccus* spp. (25D6, 25D3, 25H3) and *Enterococcus* genus.

Example 4

Combination of the selected antigens (25D6, 25D3, 25H3 and 26C6) have been tested in the same conditions example 2 on the same panel of samples, in order to improve sensibility and/or specificity of the diagnosing method according to the invention.

TABLE 3

Results (LUMINEX ® technology) obtained by testing combination of antigens for *Viridans streptococci*.

| Ratio of positive sera | 25C6 | 25D6-25H3-25C6 |
|---|---|---|
| Viridans *streptococci* positive patients (5) | 50% | 100% |
| Healthy prosthesis carriers (22) | 0% | 9% |
| Infected prosthesis patients with other infections than *streptococci*, *enterococci*, or *Peptostreptococcus* spp. (31) | 16% | 32% |

TABLE 4

Results (LUMINEX ® technology) obtained by testing combination of antigens for *Peptostreptococcus*.

| Ratio of positive sera | 25D6 | 25D6-25D3 |
|---|---|---|
| *Peptostreptococcus* positive patients (2) | 100% | 100% |
| Healthy prosthesis carriers (22) | 14% | 0% |
| Infected prosthesis patients with other infections than *streptococci*, *enterococci*, or *Peptostreptococcus* spp . . . (31) | 23% | 13% |

TABLE 5

Results (LUMINEX ® technology) obtained by testing combination of antigens for *Enterococcus faecalis*.

| Ratio of positive sera | 25C6 | 25D6-25D3-25H3-25C6 |
|---|---|---|
| *Enterococcus faecalis* positive patients (3) | 33% | 33% |
| Healthy prosthesis carriers (22) | 0% | 0% |
| Infected prosthesis patients with other infections than *streptococci*, *enterococci*, or *Peptostreptococcus* spp . . . (31) | 16% | 10% |

TABLE 6

Results (LUMINEX ® technology) obtained by testing combination of antigens for Beta hemolytic *streptococci*.

| Ratio of positive sera | 25D3 | 25D6-25D3-25H3-25C6 |
|---|---|---|
| Beta hemolytic *streptococci* positive patients (16) | 87% | 80% |
| Healthy prosthesis carriers (22) | 5% | 0% |
| Infected prosthesis patients with other infections than *streptococci*, *enterococci*, or *Peptostreptococcus* spp . . . (31) | 19% | 13% |

By comparing results obtained by using antigens combinations with best results obtained by testing one antigen, a clear improvement of the diagnosis method according to the invention is observed. Indeed, the combination of antigens (see tables 3 to 6) clearly provides an improvement in the sensibility and/or in the specificity of the test by increasing detection of positive tested patients (right positive) (see table 3) or reducing false positive detection (see table 4 to 6).

What is claimed is:

1. An in vitro method of determining if an individual having an implanted prosthetic material is infected by a *Streptococcus*, *Enterococcus*, or *Peptostreptococcus* bacterium, the method comprising:

(a) detecting antibodies specific to the protein of at least one of SEQ ID NO: 2, SEQ ID NO: 4, SEQ ID NO: 6, and SEQ ID NO: 8 in a biological sample of the individual, wherein the biological sample is selected from the group consisting of blood, serum, plasma, saliva, urine, cerebrospinal fluid, pleural fluid, and articular fluid and (b) deducing therefrom that the individual is infected by the *Streptococcus*, the *Enterococcus*, or the *Peptostrepto*-

*coccus* bacterium when the antibodies specific to the protein of at least one of SEQ ID NO: 4 and SEQ ID NO: 6 are detected;

deducing therefrom that the individual is infected by the *Streptococcus*, or the *Peptostreptococcus* bacterium when the antibodies specific to the protein of SEQ ID NO: 2 are detected and deducing therefrom that the individual is infected by the *Streptococcus*, or the *Enterococcus* bacterium when the antibodies specific to the protein of SEQ ID NO: 8 are detected.

2. The method of claim 1, wherein the *Streptococcus* bacterium is selected from the group consisting of beta-hemolytic *Streptococcus* and *Viridans Streptococcus*; the *Enterococcus* bacterium is selected from the group consisting of *Enterococcus faecium* and *Enterococcus faecalis*; or the *Peptostreptococcus* bacterium is selected from the group consisting of *Peptostreptococcus magnus*, *Peptostreptococcus asaccharolyticus*, *Peptostreptococcus anaerobius*, *Peptostreptococcus prevotii*, and *Peptostreptococcus micros*.

3. The method of claim 2, wherein the beta-hemolytic *Streptococcus* is selected from the group consisting of *Streptococcus pyogenes*, *Streptococcus agalactiae*, *Streptococcus alactolyticus* and *Streptococcus dysagalactiae*.

4. The method of claim 2, wherein the *Viridans Streptococcus* is selected from the group consisting of *Streptococcus mitis*, *Streptococcus oralis*, *Streptococcus sanguis*, *Streptococcus parasanguis*, and *Streptococcus gordonii*.

5. The method of claim 1, wherein the detected antibodies are IgG.

6. The method of claim 1, wherein the implanted prosthetic material infected by the bacterium is a prosthetic joint implanted in the individual.

7. The method of claim 1, wherein the implanted prosthetic material in the individual infected is a knee joint, a shoulder joint, or a hip joint.

8. The method of claim 1, wherein the individual is under antibiotic treatment.

9. An in vitro method of determining if an individual having an implanted prosthetic material is infected by a *Streptococcus*, *Enterococcus*, or *Peptostreptococcus* bacterium, the method comprising:

(a) contacting capture ligands specific to the protein of at least one of SEQ ID NO: 2, SEQ ID NO: 4, SEQ ID NO: 6, and SEQ ID NO: 8 in a biological sample of the individual, wherein the biological sample is selected from the group consisting of blood, serum, plasma, saliva, urine, cerebrospinal fluid, pleural fluid, and articular fluid and (b) determining if said protein is bound to the specific capture ligands and (c) deducing therefrom that the individual is infected by the *Streptococcus*, the *Enterococcus*, or the *Peptostreptococcus* bacterium, when the capture ligands specific to the protein of at least one of SEQ ID NO: 4 and SEQ ID NO: 6 are detected;

deducing therefrom that the individual is infected by the *Streptococcus*, or the *Peptostreptococcus* bacterium when the capture ligands specific to the protein of SEQ ID NO: 2 are detected and deducing therefrom that the individual is infected by the *Streptococcus*, or the *Enterococcus* bacterium when the capture ligands specific to the protein of SEQ ID NO: 8 are detected, wherein the prosthetic material implanted in the individual is infected by said bacterium.

* * * * *

SEQUENCE LISTING

<160> NUMBER OF SEQ ID NOS: 24

<210> SEQ ID NO 1
<211> LENGTH: 1143
<212> TYPE: DNA
<213> ORGANISM: Streptococcus agalactiae

<400> SEQUENCE: 1

```
gcttcaaaaa caactatcaa actttgggtc ccaacagatt caaaagcgtc ttataaagca      60
attgttaaaa aattcgagaa ggaaaacaaa ggcgttactg taaaaatgat tgagtctaat     120
gactccaaag ctcaagaaaa cgtaaaaaaa gacccaagca aggcagccga tgtattctca     180
```

| | | |
|---|---|---|
| cttccacatg accaacttgg tcaattagta gaatctggtg ttatccaaga aattccagag | 240 |
| caatactcaa aagaaattgc taaaaacgac actaaacaat cacttactgg tgcacaatat | 300 |
| aaagggaaaa cttatgcatt cccatttggt attgaatctc aagttcttta ttataataaa | 360 |
| acaaagttaa ctgctgacga cgttaaatca tacgaaacaa ttacaagcaa agggaaattc | 420 |
| ggtcaacagc ttaaagcagc taactcatat gtaacaggtc ctcttttcct ttctgtaggc | 480 |
| gacactttat ttggtaaatc tggtgaagat gccaaaggca ctaactgggg taatgaagca | 540 |
| ggtgtttctg tccttaaatg gattgcagat caaagaaaaa atgatggttt tgtcaacttg | 600 |
| acagctgaaa atacaatgtc taaatttggc gatggttctg ttcatgcttt tgaaagtgga | 660 |
| ccatgggatt acgacgctgc taaaaaagct gtcggtgaag ataaaatcgg tgttgctgtt | 720 |
| tacccaacaa tgaaaatcgg tgacaaagaa gttcaacaaa aagcattctt gggcgttaaa | 780 |
| ctttatgccg ttaaccaagc acctgctggt tcaaacacta aacgaatctc agctagctac | 840 |
| aaactcgctg catatctaac taatgctgaa agtcaaaaaa ttcaattcga aaacgtcat | 900 |
| atcgttcctg ctaactcatc aattcaatct tctgatagcg tccaaaaaga tgaacttgca | 960 |
| aaagcagtta tcgaaatggg tagctcagat aaatatacaa cggttatgcc taagttgagt | 1020 |
| caaatgtcaa cattctggac agaaagtgct gctattctta gcgatactta cagtggtaaa | 1080 |
| atcaaatcta gcgattacct taaacgtcta aacaattcg ataaagacat cgctaaaaca | 1140 |
| aaa | 1143 |

<210> SEQ ID NO 2
<211> LENGTH: 381
<212> TYPE: PRT
<213> ORGANISM: Streptococcus agalactiae

<400> SEQUENCE: 2

```
Ala Ser Lys Thr Thr Ile Lys Leu Trp Val Pro Thr Asp Ser Lys Ala
1               5                   10                  15

Ser Tyr Lys Ala Ile Val Lys Lys Phe Glu Lys Glu Asn Lys Gly Val
            20                  25                  30

Thr Val Lys Met Ile Glu Ser Asn Asp Ser Lys Ala Gln Glu Asn Val
        35                  40                  45

Lys Lys Asp Pro Ser Lys Ala Ala Asp Val Phe Ser Leu Pro His Asp
    50                  55                  60

Gln Leu Gly Gln Leu Val Glu Ser Gly Val Ile Gln Glu Ile Pro Glu
65                  70                  75                  80

Gln Tyr Ser Lys Glu Ile Ala Lys Asn Asp Thr Lys Gln Ser Leu Thr
                85                  90                  95

Gly Ala Gln Tyr Lys Gly Lys Thr Tyr Ala Phe Pro Phe Gly Ile Glu
            100                 105                 110

Ser Gln Val Leu Tyr Tyr Asn Lys Thr Lys Leu Thr Ala Asp Asp Val
        115                 120                 125

Lys Ser Tyr Glu Thr Ile Thr Ser Lys Gly Lys Phe Gly Gln Gln Leu
    130                 135                 140

Lys Ala Ala Asn Ser Tyr Val Thr Gly Pro Leu Phe Leu Ser Val Gly
145                 150                 155                 160

Asp Thr Leu Phe Gly Lys Ser Gly Glu Asp Ala Lys Gly Thr Asn Trp
                165                 170                 175

Gly Asn Glu Ala Gly Val Ser Val Leu Lys Trp Ile Ala Asp Gln Lys
            180                 185                 190
```

```
                Lys Asn Asp Gly Phe Val Asn Leu Thr Ala Glu Asn Thr Met Ser Lys
                            195                 200                 205

Phe Gly Asp Gly Ser Val His Ala Phe Glu Ser Gly Pro Trp Asp Tyr
                        210                 215                 220

Asp Ala Ala Lys Lys Ala Val Gly Glu Asp Lys Ile Gly Val Ala Val
                225                 230                 235                 240

Tyr Pro Thr Met Lys Ile Gly Asp Lys Glu Val Gln Gln Lys Ala Phe
                                245                 250                 255

Leu Gly Val Lys Leu Tyr Ala Val Asn Gln Ala Pro Ala Gly Ser Asn
                            260                 265                 270

Thr Lys Arg Ile Ser Ala Ser Tyr Lys Leu Ala Ala Tyr Leu Thr Asn
                        275                 280                 285

Ala Glu Ser Gln Lys Ile Gln Phe Glu Lys Arg His Ile Val Pro Ala
                290                 295                 300

Asn Ser Ser Ile Gln Ser Ser Asp Ser Val Gln Lys Asp Glu Leu Ala
                305                 310                 315                 320

Lys Ala Val Ile Glu Met Gly Ser Ser Asp Lys Tyr Thr Thr Val Met
                                325                 330                 335

Pro Lys Leu Ser Gln Met Ser Thr Phe Trp Thr Glu Ser Ala Ala Ile
                            340                 345                 350

Leu Ser Asp Thr Tyr Ser Gly Lys Ile Lys Ser Ser Asp Tyr Leu Lys
                        355                 360                 365

Arg Leu Lys Gln Phe Asp Lys Asp Ile Ala Lys Thr Lys
                370                 375                 380

<210> SEQ ID NO 3
<211> LENGTH: 1458
<212> TYPE: DNA
<213> ORGANISM: Streptococcus agalactiae

<400> SEQUENCE: 3
gcagaaacta ttaatccaga aacaagcctg acaatggcaa cagcatcaac agaaagttct    60
tctgaagcag agaaacagga aaaaacacaa cctacagatt cagaaactgc ttcaccttca   120
gccgaaggaa gtatctcaac agaaaaaaca gagattggta cgacagagac atcatcaagc   180
aatgaatcat catcaagttc atcacatcaa tcttcttcca acgaagatgc taaaacatct   240
gattctgctt caacagcatc tactcctagc actaatacta caaacagtag tcaagcagac   300
agtaagccag gtcaatcaac aaagactgaa ttaaaacctg agcctacctt accattagta   360
gagcctaaaa taactcccgc tccgtctcag atagaaagtg ttcagacaaa tcagaatgct   420
tctgttcctg ctttatcctt tgatgataac ttattatcaa caccgatttc accagtgaca   480
gcaacgccat tctacgtaga acactggtct ggtcaggatg cctactctca ctatttattg   540
tcacatcgtt acggtatcaa agctgaacaa ttagatgggt acttaaaatc tttagggatt   600
caatatgatt ctaatcgtat caatggtgct aagttattac aatgggaaaa agatagtggt   660
ttagatgtcc gtgctattgt agctattgct gtccttgaaa gttcattggg aactcaaggg   720
gtggctaaga tgccaggtgc taatatgttt ggttatggtg cctttgatca tgactctagc   780
catgctagtg cttataatga tgaagaagca attatgttgt tgacaaaaaa tacaattatt   840
aaaaacaaca actctagctt tgaaatccaa gatttgaaag cacagaaatt atcttctgga   900
caacttaata cagttactga gggtggtgtt tattatacag ataactctgg aactggtaaa   960
cgtcgtgccc agattatgga agatttagac cgctggattg atcaacatgg agggacacca  1020
gaaattcctg ctgccttgaa agctttatcg acagcaagtt tagcagattt accaagtggt  1080
```

```
tttagcttat caacagcagt taacacagct agctatattg catcaactta tccatggggt    1140
gaatgtacat ggtatgtctt taaccgagct aaagagttag gttatacatt tgatccattt    1200
atgggtaatg gtggagattg gcaacataag gctggttttg aaacaacaca ttcaccaaaa    1260
gtaggctatg ctgtatcatt ttcaccagga caagctggtg ctgatggcac ttacggtcac    1320
gtagctattg ttgaagaagt taaaaagat ggttcagttc ttatttcaga atctaatgca    1380
atgggacgtg gtattgtctc ttaccgtact tttagttcag cacaagctgc acaattaact    1440
tatgttattg gccataaa                                                  1458
```

<210> SEQ ID NO 4
<211> LENGTH: 486
<212> TYPE: PRT
<213> ORGANISM: Streptococcus agalactiae

<400> SEQUENCE: 4

```
Ala Glu Thr Ile Asn Pro Glu Thr Ser Leu Thr Met Ala Thr Ala Ser
1               5                   10                  15

Thr Glu Ser Ser Ser Glu Ala Glu Lys Gln Glu Lys Thr Gln Pro Thr
            20                  25                  30

Asp Ser Glu Thr Ala Ser Pro Ser Ala Glu Gly Ser Ile Ser Thr Glu
        35                  40                  45

Lys Thr Glu Ile Gly Thr Thr Glu Thr Ser Ser Asn Glu Ser Ser
    50                  55                  60

Ser Ser Ser Ser His Gln Ser Ser Asn Glu Asp Ala Lys Thr Ser
65                  70                  75                  80

Asp Ser Ala Ser Thr Ala Ser Thr Pro Ser Thr Asn Thr Asn Ser
                85                  90                  95

Ser Gln Ala Asp Ser Lys Pro Gly Gln Ser Thr Lys Thr Glu Leu Lys
            100                 105                 110

Pro Glu Pro Thr Leu Pro Leu Val Glu Pro Lys Ile Thr Pro Ala Pro
        115                 120                 125

Ser Gln Ile Glu Ser Val Gln Thr Asn Gln Asn Ala Ser Val Pro Ala
    130                 135                 140

Leu Ser Phe Asp Asp Asn Leu Leu Ser Thr Pro Ile Ser Pro Val Thr
145                 150                 155                 160

Ala Thr Pro Phe Tyr Val Glu His Trp Ser Gly Gln Asp Ala Tyr Ser
                165                 170                 175

His Tyr Leu Leu Ser His Arg Tyr Gly Ile Lys Ala Glu Gln Leu Asp
            180                 185                 190

Gly Tyr Leu Lys Ser Leu Gly Ile Gln Tyr Asp Ser Asn Arg Ile Asn
        195                 200                 205

Gly Ala Lys Leu Leu Gln Trp Glu Lys Asp Ser Gly Leu Asp Val Arg
    210                 215                 220

Ala Ile Val Ala Ile Ala Val Leu Glu Ser Ser Leu Gly Thr Gln Gly
225                 230                 235                 240

Val Ala Lys Met Pro Gly Ala Asn Met Phe Gly Tyr Gly Ala Phe Asp
                245                 250                 255

His Asp Ser Ser His Ala Ser Ala Tyr Asn Asp Glu Glu Ala Ile Met
            260                 265                 270

Leu Leu Thr Lys Asn Thr Ile Ile Lys Asn Asn Asn Ser Ser Phe Glu
        275                 280                 285

Ile Gln Asp Leu Lys Ala Gln Lys Leu Ser Ser Gly Gln Leu Asn Thr
    290                 295                 300
```

```
Val Thr Glu Gly Gly Val Tyr Tyr Thr Asp Asn Ser Gly Thr Gly Lys
305                 310                 315                 320

Arg Arg Ala Gln Ile Met Glu Asp Leu Asp Arg Trp Ile Asp Gln His
            325                 330                 335

Gly Gly Thr Pro Glu Ile Pro Ala Ala Leu Lys Ala Leu Ser Thr Ala
            340                 345                 350

Ser Leu Ala Asp Leu Pro Ser Gly Phe Ser Leu Ser Thr Ala Val Asn
            355                 360                 365

Thr Ala Ser Tyr Ile Ala Ser Thr Tyr Pro Trp Gly Glu Cys Thr Trp
370                 375                 380

Tyr Val Phe Asn Arg Ala Lys Glu Leu Gly Tyr Thr Phe Asp Pro Phe
385                 390                 395                 400

Met Gly Asn Gly Gly Asp Trp Gln His Lys Ala Gly Phe Glu Thr Thr
                405                 410                 415

His Ser Pro Lys Val Gly Tyr Ala Val Ser Phe Ser Pro Gly Gln Ala
            420                 425                 430

Gly Ala Asp Gly Thr Tyr Gly His Val Ala Ile Val Glu Glu Val Lys
            435                 440                 445

Lys Asp Gly Ser Val Leu Ile Ser Glu Ser Asn Ala Met Gly Arg Gly
450                 455                 460

Ile Val Ser Tyr Arg Thr Phe Ser Ser Ala Gln Ala Ala Gln Leu Thr
465                 470                 475                 480

Tyr Val Ile Gly His Lys
                485

<210> SEQ ID NO 5
<211> LENGTH: 1230
<212> TYPE: DNA
<213> ORGANISM: Streptococcus agalactiae

<400> SEQUENCE: 5
gcacaagaaa cagatacgac gtggacagca cgtactgttt cagaggtaaa ggctgatttg      60
gtaaagcaag acaataaatc atcatatact gtgaaatatg gtgatacact aagcgttatt     120
tcagaagcaa tgtcaattga tatgaatgtc ttagcaaaaa taataacat tgcagatatc      180
aatcttattt atcctgagac aacactgaca gtaacttacg atcagaagag tcatactgcc     240
acttcaatga aaatagaaac accagcaaca atgctgctg tcaaacaac agctactgtg       300
gatttgaaaa ccaatcaagt ttctgttgca gaccaaaaag tttctctcaa tacaatttcg     360
gaaggtatga caccagaagc agcaacaacg attgtttcgc caatgaagac atattcttct    420
gcgccagctt tgaaatcaaa agaagtatta gcacaagagc aagctgttag tcaagcagca     480
gctaatgaac aggtatcacc agctcctgtg aagtcgatta cttcagaagt tccagcagct     540
aaagaggaag ttaaaccaac tcagacgtca gtcagtcagt caacaacagt atcaccagct     600
tctgttgccg ctgaaacacc agctccagta gctaaagtag caccggtaag aactgtagca     660
gcccctagag tggcaagtgt taagtagtc actcctaaag tagaaactgg tgcatcacca     720
gagcatgtat cagctccagc agttcctgtg actacgactt caccagctac agacagtaag     780
ttacaagcga ctgaagttaa gagcgttccg gtagcacaaa aagctccaac agcaacaccg     840
gtagcacaac cagcttcaac aacaaatgca gtagctgcac atcctgaaaa tgcagggctc     900
caacctcatg ttcagctta taagaaaaaa gtagcgtcaa cttatggagt taatgaattc     960
agtacatacc gtgcgggaga tccaggtgat catggtaaag gtttagcagt tgactttatt    1020
```

```
gtaggtacta atcaagcact tggtaataaa gttgcacagt actctacaca aaatatggca    1080
gcaaataaca tttcatatgt tatctggcaa caaaagtttt actcaaatac aaacagtatt    1140
tatggacctg ctaatacttg gaatgcaatg ccagatcgtg gtggcgttac tgccaaccac    1200
tatgaccacg ttcacgtatc atttaacaaa                                     1230
```

<210> SEQ ID NO 6
<211> LENGTH: 410
<212> TYPE: PRT
<213> ORGANISM: Streptococcus agalactiae

<400> SEQUENCE: 6

```
Ala Gln Glu Thr Asp Thr Thr Trp Thr Ala Arg Thr Val Ser Glu Val
1               5                  10                  15

Lys Ala Asp Leu Val Lys Gln Asp Asn Lys Ser Ser Tyr Thr Val Lys
            20                  25                  30

Tyr Gly Asp Thr Leu Ser Val Ile Ser Glu Ala Met Ser Ile Asp Met
        35                  40                  45

Asn Val Leu Ala Lys Ile Asn Asn Ile Ala Asp Ile Asn Leu Ile Tyr
    50                  55                  60

Pro Glu Thr Thr Leu Thr Val Thr Tyr Asp Gln Lys Ser His Thr Ala
65                  70                  75                  80

Thr Ser Met Lys Ile Glu Thr Pro Ala Thr Asn Ala Ala Gly Gln Thr
                85                  90                  95

Thr Ala Thr Val Asp Leu Lys Thr Asn Gln Val Ser Val Ala Asp Gln
            100                 105                 110

Lys Val Ser Leu Asn Thr Ile Ser Glu Gly Met Thr Pro Glu Ala Ala
        115                 120                 125

Thr Thr Ile Val Ser Pro Met Lys Thr Tyr Ser Ser Ala Pro Ala Leu
    130                 135                 140

Lys Ser Lys Glu Val Leu Ala Gln Gln Ala Val Ser Gln Ala Ala
145                 150                 155                 160

Ala Asn Glu Gln Val Ser Pro Ala Pro Val Lys Ser Ile Thr Ser Glu
                165                 170                 175

Val Pro Ala Ala Lys Glu Glu Val Lys Pro Thr Gln Thr Ser Val Ser
            180                 185                 190

Gln Ser Thr Thr Val Ser Pro Ala Ser Val Ala Ala Glu Thr Pro Ala
        195                 200                 205

Pro Val Ala Lys Val Ala Pro Val Arg Thr Val Ala Ala Pro Arg Val
    210                 215                 220

Ala Ser Val Lys Val Val Thr Pro Lys Val Glu Thr Gly Ala Ser Pro
225                 230                 235                 240

Glu His Val Ser Ala Pro Ala Val Pro Val Thr Thr Thr Ser Pro Ala
                245                 250                 255

Thr Asp Ser Lys Leu Gln Ala Thr Glu Val Lys Ser Val Pro Val Ala
            260                 265                 270

Gln Lys Ala Pro Thr Ala Thr Pro Val Ala Gln Pro Ala Ser Thr Thr
        275                 280                 285

Asn Ala Val Ala Ala His Pro Glu Asn Ala Gly Leu Gln Pro His Val
    290                 295                 300

Ala Ala Tyr Lys Glu Lys Val Ala Ser Thr Tyr Gly Val Asn Glu Phe
305                 310                 315                 320

Ser Thr Tyr Arg Ala Gly Asp Pro Gly Asp His Gly Lys Gly Leu Ala
                325                 330                 335
```

```
Val Asp Phe Ile Val Gly Thr Asn Gln Ala Leu Gly Asn Lys Val Ala
            340                 345                 350

Gln Tyr Ser Thr Gln Asn Met Ala Ala Asn Asn Ile Ser Tyr Val Ile
        355                 360                 365

Trp Gln Gln Lys Phe Tyr Ser Asn Thr Asn Ser Ile Tyr Gly Pro Ala
    370                 375                 380

Asn Thr Trp Asn Ala Met Pro Asp Arg Gly Gly Val Thr Ala Asn His
385                 390                 395                 400

Tyr Asp His Val His Val Ser Phe Asn Lys
                405                 410

<210> SEQ ID NO 7
<211> LENGTH: 681
<212> TYPE: DNA
<213> ORGANISM: Streptococcus agalactiae

<400> SEQUENCE: 7
gctgatcaag tgacaactcc acaagtggta aatcatgtaa acagtaataa tcaagcccag      60
caaatggctc aaaagcttga tcaagatagc attcagttga aaatatcaa agataatgtt     120 cagggaacag attatgaaaa aacggttaat gaggctatta ctagtgttga aaaattaaag     180
acttcattgc gtgccaaccc tgagacagtt tatgatttga attctattgg tagtcgtgta     240
gaagccttaa cagatgtgat tgaagcaatc acttttttca ctcaacattt agcaaataag     300
gttagtcaag caaatattga tatgggattt gggataacta agctggttat tcgcatttta     360
gatccatttg cttcagttga ttcaattaaa gctcaagtta acgatgtaaa ggcattagaa     420
caaaaggttt taacttatcc tgatttaaaa ccaactgata gagctaccat ctatacaaaa     480
tcaaaacttg ataaggaaat ctggaataca cgctttacta gagataaaaa agtacttaac     540
gtcaaagaat ttaaagtttta caatacttta aataaagcaa tcacacatgc tgttggagtt     600
cagttgaatc caaatgttac ggtacaacaa gttgatcaag agattgtaac attacaagca     660
gcacttcaaa cagcattaaa a                                              681

<210> SEQ ID NO 8
<211> LENGTH: 227
<212> TYPE: PRT
<213> ORGANISM: Streptococcus agalactiae

<400> SEQUENCE: 8

Ala Asp Gln Val Thr Thr Pro Gln Val Val Asn His Val Asn Ser Asn
1               5                   10                  15

Asn Gln Ala Gln Gln Met Ala Gln Lys Leu Asp Gln Asp Ser Ile Gln
            20                  25                  30

Leu Arg Asn Ile Lys Asp Asn Val Gln Gly Thr Asp Tyr Glu Lys Thr
        35                  40                  45

Val Asn Glu Ala Ile Thr Ser Val Glu Lys Leu Lys Thr Ser Leu Arg
    50                  55                  60

Ala Asn Pro Glu Thr Val Tyr Asp Leu Asn Ser Ile Gly Ser Arg Val
65                  70                  75                  80

Glu Ala Leu Thr Asp Val Ile Glu Ala Ile Thr Phe Ser Thr Gln His
                85                  90                  95

Leu Ala Asn Lys Val Ser Gln Ala Asn Ile Asp Met Gly Phe Gly Ile
            100                 105                 110

Thr Lys Leu Val Ile Arg Ile Leu Asp Pro Phe Ala Ser Val Asp Ser
        115                 120                 125
```

```
Ile Lys Ala Gln Val Asn Asp Val Lys Ala Leu Glu Gln Lys Val Leu
130                 135                 140
Thr Tyr Pro Asp Leu Lys Pro Thr Asp Arg Ala Thr Ile Tyr Thr Lys
145                 150                 155                 160
Ser Lys Leu Asp Lys Glu Ile Trp Asn Thr Arg Phe Thr Arg Asp Lys
                165                 170                 175
Lys Val Leu Asn Val Lys Glu Phe Lys Val Tyr Asn Thr Leu Asn Lys
                180                 185                 190
Ala Ile Thr His Ala Val Gly Val Gln Leu Asn Pro Asn Val Thr Val
            195                 200                 205
Gln Gln Val Asp Gln Glu Ile Val Thr Leu Gln Ala Ala Leu Gln Thr
210                 215                 220
Ala Leu Lys
225

<210> SEQ ID NO 9
<211> LENGTH: 1500
<212> TYPE: DNA
<213> ORGANISM: Streptococcus agalactiae

<400> SEQUENCE: 9
ggggaaagta ccgtaccgga aaatggtgct aaaggaaagt tagttgttaa aaagacagat      60
gaccagaaca aaccactttc aaaagctacc tttgttttaa aaactactgc tcatccagaa     120
agtaaaatag aaaaagtaac tgctgagcta acaggtgaag ctactttga taatctcata     180 cctggaggtt atactttatc agaagaaaca gcgcccgaag ttataaaaa gactaaccag     240 acttggcaag ttaaggttga gagtaatgga aaaactacga tacaaaatag tggtgataaa     300
aattccacaa ttggacaaaa tcacgaagaa ctagataagc agtatccccc cacaggaatt     360
tatgaagata caaaggaatc ttataaactt gagcatgtta aaggttcagt tccaaatgga     420
aagtcagagg caaaagcagt taacccatat tcaagtgaag gtgagcatat aagagaaatt     480
ccagagggaa cattatctaa acgtatttca gaagtaggtg atttagctca taataaatat     540
aaaattgagt taactgtcag tggaaaaacc atagtaaaac cagtggacaa acaaaagccg     600
ttagatgttg tcttcgtact cgataattct aactcaatga ataacgatgg cccaaatttt     660
caaaggcata taaagccaa gaaagctgcc gaagctcttg ggaccgcagt aaaagatatt     720
ttaggagcaa acagtgataa tagggttgca ttagttacct atggttcaga tattttttgat     780 ggtaggagtg tagatgtcgt aaaaggattt aaagaagatg ataaatatta tggccttcaa     840
actaagttca caattcagac agagaattat agtcataaac aattaacaaa taatgctgaa     900
gagattataa aaaggattcc tacagaagct cctagagcta atggggatc aactacaaac     960 ggacttactc cagagcaaca aaagcagtac tatcttagta agtagggga acatttact    1020 atgaaagcct tcatggaggc agatgatatt ttgagtcaag tagatcgaaa tagtcaaaaa    1080
attattgttc atataactga tggtgttcca acaagatcat atgctattaa taattttaaa    1140
ttgggtgcat catatgaaag ccaatttgaa caaatgaaaa aaaatggata tctaaataaa    1200
agtaattttc tacttactga taagcccgag gatataaaag gaaatgggga gagttacttt    1260
ttgtttccct tagatagtta tcaaacacag ataatctctg gaaacttaca aaaacttcat    1320
tatttagatt taaatcttaa ttaccctaaa ggtacaattt atcgaaatgg accagtaaga    1380
gaacatggaa caccaaccaa acttatatata aatagtttaa aacagaaaaa ttatgacatc    1440
tttaattttg gtatagatat atctgctttt agacaagttt ataatgagga ttataagaaa    1500
```

<210> SEQ ID NO 10
<211> LENGTH: 500
<212> TYPE: PRT
<213> ORGANISM: Streptococcus agalactiae

<400> SEQUENCE: 10

```
Gly Glu Ser Thr Val Pro Glu Asn Gly Ala Lys Gly Lys Leu Val Val
1               5                   10                  15

Lys Lys Thr Asp Asp Gln Asn Lys Pro Leu Ser Lys Ala Thr Phe Val
            20                  25                  30

Leu Lys Thr Thr Ala His Pro Glu Ser Lys Ile Glu Lys Val Thr Ala
        35                  40                  45

Glu Leu Thr Gly Glu Ala Thr Phe Asp Asn Leu Ile Pro Gly Gly Tyr
    50                  55                  60

Thr Leu Ser Glu Glu Thr Ala Pro Glu Gly Tyr Lys Lys Thr Asn Gln
65                  70                  75                  80

Thr Trp Gln Val Lys Val Glu Ser Asn Gly Lys Thr Thr Ile Gln Asn
                85                  90                  95

Ser Gly Asp Lys Asn Ser Thr Ile Gly Gln Asn His Glu Glu Leu Asp
            100                 105                 110

Lys Gln Tyr Pro Pro Thr Gly Ile Tyr Glu Asp Thr Lys Glu Ser Tyr
        115                 120                 125

Lys Leu Glu His Val Lys Gly Ser Val Pro Asn Gly Lys Ser Glu Ala
    130                 135                 140

Lys Ala Val Asn Pro Tyr Ser Ser Glu Gly Glu His Ile Arg Glu Ile
145                 150                 155                 160

Pro Glu Gly Thr Leu Ser Lys Arg Ile Ser Glu Val Gly Asp Leu Ala
                165                 170                 175

His Asn Lys Tyr Lys Ile Glu Leu Thr Val Ser Gly Lys Thr Ile Val
            180                 185                 190

Lys Pro Val Asp Lys Gln Lys Pro Leu Asp Val Val Phe Val Leu Asp
        195                 200                 205

Asn Ser Asn Ser Met Asn Asn Asp Gly Pro Asn Phe Gln Arg His Asn
    210                 215                 220

Lys Ala Lys Lys Ala Ala Glu Ala Leu Gly Thr Ala Val Lys Asp Ile
225                 230                 235                 240

Leu Gly Ala Asn Ser Asp Asn Arg Val Ala Leu Val Thr Tyr Gly Ser
                245                 250                 255

Asp Ile Phe Asp Gly Arg Ser Val Asp Val Lys Gly Phe Lys Glu
            260                 265                 270

Asp Asp Lys Tyr Tyr Gly Leu Gln Thr Lys Phe Thr Ile Gln Thr Glu
        275                 280                 285

Asn Tyr Ser His Lys Gln Leu Thr Asn Asn Ala Glu Glu Ile Ile Lys
    290                 295                 300

Arg Ile Pro Thr Glu Ala Pro Arg Ala Lys Trp Gly Ser Thr Thr Asn
305                 310                 315                 320

Gly Leu Thr Pro Glu Gln Gln Lys Gln Tyr Tyr Leu Ser Lys Val Gly
                325                 330                 335

Glu Thr Phe Thr Met Lys Ala Phe Met Glu Ala Asp Asp Ile Leu Ser
            340                 345                 350

Gln Val Asp Arg Asn Ser Gln Lys Ile Ile Val His Ile Thr Asp Gly
        355                 360                 365

Val Pro Thr Arg Ser Tyr Ala Ile Asn Asn Phe Lys Leu Gly Ala Ser
    370                 375                 380
```

```
Tyr Glu Ser Gln Phe Glu Gln Met Lys Lys Asn Gly Tyr Leu Asn Lys
385                 390                 395                 400

Ser Asn Phe Leu Leu Thr Asp Lys Pro Glu Asp Ile Lys Gly Asn Gly
            405                 410                 415

Glu Ser Tyr Phe Leu Phe Pro Leu Asp Ser Tyr Gln Thr Gln Ile Ile
        420                 425                 430

Ser Gly Asn Leu Gln Lys Leu His Tyr Leu Asp Leu Asn Leu Asn Tyr
    435                 440                 445

Pro Lys Gly Thr Ile Tyr Arg Asn Gly Pro Val Arg Glu His Gly Thr
450                 455                 460

Pro Thr Lys Leu Tyr Ile Asn Ser Leu Lys Gln Lys Asn Tyr Asp Ile
465                 470                 475                 480

Phe Asn Phe Gly Ile Asp Ile Ser Ala Phe Arg Gln Val Tyr Asn Glu
                485                 490                 495

Asp Tyr Lys Lys
            500

<210> SEQ ID NO 11
<211> LENGTH: 1618
<212> TYPE: DNA
<213> ORGANISM: Streptococcus agalactiae

<400> SEQUENCE: 11
gctgactcga acaaacaaaa cactgccaat acagaaacca caacgacaaa tgaacaacca      60
aaaccagaaa gtagtgagct aactacagaa aaagcaggtc agaaaatgga tgatatgctt     120
aactctaacg atatgattaa gcttgctccc aaagaaatgc cactagaatc tgcagaaaaa     180
gaagaaaaaa agtcagaaga caataaaaaa agcgaagaag atcatactga gaaaatcaat     240
gacaagattt attcactaaa ttataatgag cttgaagtac ttgctaaaaa tggtgaaacc     300
attgaaaact ttgttcctaa agaaggcgtt aagaaagctg acaaatttat tgtcattgaa     360
agaaagaaaa aaaatatcaa cactacaccg gtcgatattt ccatcattga ctctgtcact     420
gataggacct atccagcagc ccttcagctg gctaataaag gttttaccga aaacaaacca     480
gacgcagtag tcaccaagcg aaacccacaa aaaatcccata ttgatttacc aggtatggga     540
gacaaagcaa cggttgaggt caatgaccct acctatgcca atgtttcaac agctattgat     600
aatcttgtta accaatggca tgataattat tctggtggta atacgcttcc tgccagaaca     660
caatatactg aatcaatggt atattctaaa tcacagattg aagcagctct aaatgttaat     720
agtaaaatct tagatggtac tttaggcatt gatttcaagt cgatttcaaa aggtgaaaag     780
aaggtgatga ttgcagcata caagcaaatt ttttacaccg tatcagcaaa ccttcctaat     840
aatcctgcgg atgtgtttga taaatcagtg acctttaaag agttgcaacg aaaaggtgtc     900
agcaatgaag ccccgccact ctttgtgagt aacgtagctt atggtcgaac tgttttttgtc     960 aaactagaaa caagttctaa agtaatgat gttgaagcgg cctttagtgc agctctaaaa    1020
ggaacagatg ttaaaactaa tggaaaatac tctgatattt tagaaaatag ttcatttaca    1080
gctgtcgttt taggaggaga tgctgcagag cacaataagg tagtcacaaa agactttgat    1140
gttattagaa acgttatcaa agataatgct accttcagta gaaaaaaccc agcttatcct    1200
atttcataca ccagtgtttt ccttaaaaat aataaaattg cgggtgtcaa taacagaagt    1260
gaatacgttg aaacaacatc taccgagtac acgagtggaa aaattaacct gtctcatcaa    1320
ggtgcctatg ttgctcaata tgaaatccct tgggatgaaa tcaattatga tgacaaagga    1380
```

```
aaagaagtga ttactaaacg acgttgggac aacaactggt atagtaagac atcaccattt    1440
agcacagtta tcccactagg agctaattca cgaaatatcc gtatcatggc tagagagtgc    1500
accggcttag cttgggaatg gtggcgaaaa gtgatcgacg aaagagatgt gaaactgtct    1560
aaagaaatta atgtcaacat ctcaggatca accttgagcc catatggttc gattactt      1618
```

<210> SEQ ID NO 12
<211> LENGTH: 541
<212> TYPE: PRT
<213> ORGANISM: Streptococcus agalactiae

<400> SEQUENCE: 12

```
Ala Asp Ser Asn Lys Gln Asn Thr Ala Asn Thr Glu Thr Thr Thr Thr
1               5                   10                  15

Asn Glu Gln Pro Lys Pro Glu Ser Ser Glu Leu Thr Thr Glu Lys Ala
            20                  25                  30

Gly Gln Lys Met Asp Asp Met Leu Asn Ser Asn Asp Met Ile Lys Leu
        35                  40                  45

Ala Pro Lys Glu Met Pro Leu Glu Ser Ala Glu Lys Glu Lys Lys
    50                  55                  60

Ser Glu Asp Asn Lys Lys Ser Glu Glu Asp His Thr Glu Glu Ile Asn
65                  70                  75                  80

Asp Lys Ile Tyr Ser Leu Asn Tyr Asn Glu Leu Glu Val Leu Ala Lys
                85                  90                  95

Asn Gly Glu Thr Ile Glu Asn Phe Val Pro Lys Glu Gly Val Lys Lys
            100                 105                 110

Ala Asp Lys Phe Ile Val Ile Glu Arg Lys Lys Lys Asn Ile Asn Thr
        115                 120                 125

Thr Pro Val Asp Ile Ser Ile Ile Asp Ser Val Thr Asp Arg Thr Tyr
130                 135                 140

Pro Ala Ala Leu Gln Leu Ala Asn Lys Gly Phe Thr Glu Asn Lys Pro
145                 150                 155                 160

Asp Ala Val Val Thr Lys Arg Asn Pro Gln Lys Ile His Ile Asp Leu
                165                 170                 175

Pro Gly Met Gly Asp Lys Ala Thr Val Glu Val Asn Asp Pro Thr Tyr
            180                 185                 190

Ala Asn Val Ser Thr Ala Ile Asp Asn Leu Val Asn Gln Trp His Asp
        195                 200                 205

Asn Tyr Ser Gly Gly Asn Thr Leu Pro Ala Arg Thr Gln Tyr Thr Glu
    210                 215                 220

Ser Met Val Tyr Ser Lys Ser Gln Ile Glu Ala Ala Leu Asn Val Asn
225                 230                 235                 240

Ser Lys Ile Leu Asp Gly Thr Leu Gly Ile Asp Phe Lys Ser Ile Ser
                245                 250                 255

Lys Gly Glu Lys Lys Val Met Ile Ala Ala Tyr Lys Gln Ile Phe Tyr
            260                 265                 270

Thr Val Ser Ala Asn Leu Pro Asn Asn Pro Ala Asp Val Phe Asp Lys
        275                 280                 285

Ser Val Thr Phe Lys Glu Leu Gln Arg Lys Gly Val Ser Asn Glu Ala
    290                 295                 300

Pro Pro Leu Phe Val Ser Asn Val Ala Tyr Gly Arg Thr Val Phe Val
305                 310                 315                 320

Lys Leu Glu Thr Ser Ser Lys Ser Asn Asp Val Glu Ala Ala Phe Ser
                325                 330                 335
```

| | | | | | | | | | | | |
|---|---|---|---|---|---|---|---|---|---|---|---|
|Ala|Ala|Leu|Lys|Gly|Thr|Asp|Val|Lys|Thr|Asn|Gly|Lys|Tyr|Ser|Asp|
| | | |340| | | |345| | | |350| | | | |

Ala Ala Leu Lys Gly Thr Asp Val Lys Thr Asn Gly Lys Tyr Ser Asp
              340                 345                 350

Ile Leu Glu Asn Ser Ser Phe Thr Ala Val Val Leu Gly Gly Asp Ala
              355                 360                 365

Ala Glu His Asn Lys Val Val Thr Lys Asp Phe Asp Val Ile Arg Asn
        370                 375                 380

Val Ile Lys Asp Asn Ala Thr Phe Ser Arg Lys Asn Pro Ala Tyr Pro
385                 390                 395                 400

Ile Ser Tyr Thr Ser Val Phe Leu Lys Asn Asn Lys Ile Ala Gly Val
                405                 410                 415

Asn Asn Arg Ser Glu Tyr Val Glu Thr Thr Ser Thr Glu Tyr Thr Ser
            420                 425                 430

Gly Lys Ile Asn Leu Ser His Gln Gly Ala Tyr Val Ala Gln Tyr Glu
        435                 440                 445

Ile Leu Trp Asp Glu Ile Asn Tyr Asp Asp Lys Gly Lys Glu Val Ile
        450                 455                 460

Thr Lys Arg Arg Trp Asp Asn Asn Trp Tyr Ser Lys Thr Ser Pro Phe
465                 470                 475                 480

Ser Thr Val Ile Pro Leu Gly Ala Asn Ser Arg Asn Ile Arg Ile Met
                485                 490                 495

Ala Arg Glu Cys Thr Gly Leu Ala Trp Glu Trp Arg Lys Val Ile
            500                 505                 510

Asp Glu Arg Asp Val Lys Leu Ser Lys Glu Ile Asn Val Asn Ile Ser
        515                 520                 525

Gly Ser Thr Leu Ser Pro Tyr Gly Ser Ile Thr Tyr Lys
530                 535                 540

<210> SEQ ID NO 13
<211> LENGTH: 1530
<212> TYPE: DNA
<213> ORGANISM: Streptococcus agalactiae

<400> SEQUENCE: 13

```
atggcattaa gtcctgatat taaagaacaa cttgcccaat acctcacctt gttagaatct      60
gacctggttt tgcaagctta tcttggtgat gacgaacagt ctcaaaaggt taaagacttc     120
gtggaagaaa ttgctgcgat gtctgatcgt atttcggttg aagaaactgt cttagaccgt     180
aaaccaagct ttaaagttgc gaaaaaagga caagatagtg gggttgcctt tgctggtcta     240
cctttaggcc acgaatttac gtctttcatc cttgccctct gcaagtatc tggacgtgct      300
ccaaaagtag atcaagatgt tattgaccgc atcaaggcta ttgatcgccc actgcatttt     360
gaaacctacg tcagcttaac ctgccataac tgtccagacg ttgttcaagc tctcaacatt     420
atgtctgttt tgaatgacaa gatttcacat actatggtgg aagtggcat gttccaagat      480
gaagtgaaag caaaaggcat tatgtctgta ccaactgtct tcttagatgg tgaagaattc     540
acttcaggcc gtgctactat cgaacaactc ttagaacaag tcgctggtcc cctttcagaa     600
gaagcctttg cggataaagg ggtctatgat gtccttgttg ttggtggtgg acctgcgggc     660
aatagcgctg ctatctatgc agcccgtaaa ggattgaaaa caggtttatt ggctgagacc     720
tttggtggtc aggtcatgga aactgtcggc atcgaaaata tgattggtac cctttacact     780
gaaggaccaa aattaatggc cgaagtagag gcccatacca agtcttacga tgtggacatt     840
atcaaagcac aactagctac ttctatcgag aaaaaagaaa acatcgaggt tactctagct     900
aatggtgcgg ttttacaagc caaaactgct atttttagctc tcggtgccaa atggcgtaac     960
```

```
atcaatgttc ctggagaaga tgaattccgt aataaagggg tgacttactg ccctcactgt   1020
gatggtcctc tctttgaagg caaggacgtt gctgttatcg gtggtggaaa ctctggatta   1080
gaagctgccc ttgatttggc tggtcttgct aaacacgttt acgtgttaga attcttgcct   1140
gagctcaaag ctgacaaagt gcttcaagac cgcgcagctg atactgctaa catgactatt   1200
atcaaaaatg ttgctactaa agacattgtt ggtgacgatc atgttactgg tctcaactac   1260
actgaacgtg atagcggtga agacaaacac attgaccttg aagggtctt tgtccaaatt   1320 ggtcttgttc aaatacagc ttggctcaag gatagcggtg tgaacctaac cgaccgcggt   1380
gaaattatcg tggataaaca tgggtcaacc aatattcctg gtatctttgc tgctggggac   1440
tgtactgatt cagcttataa acaaatcatt atttcaatgg gatctggggc tactgccgcc   1500
atcggtgcct ttgactactt gattcgtcaa                                    1530

<210> SEQ ID NO 14
<211> LENGTH: 510
<212> TYPE: PRT
<213> ORGANISM: Streptococcus agalactiae

<400> SEQUENCE: 14

Met Ala Leu Ser Pro Asp Ile Lys Glu Gln Leu Ala Gln Tyr Leu Thr
1               5                   10                  15

Leu Leu Glu Ser Asp Leu Val Leu Gln Ala Tyr Leu Gly Asp Asp Glu
            20                  25                  30

Gln Ser Gln Lys Val Lys Asp Phe Val Glu Ile Ala Ala Met Ser
        35                  40                  45

Asp Arg Ile Ser Val Glu Glu Thr Val Leu Asp Arg Lys Pro Ser Phe
    50                  55                  60

Lys Val Ala Lys Lys Gly Gln Asp Ser Gly Val Ala Phe Ala Gly Leu
65                  70                  75                  80

Pro Leu Gly His Glu Phe Thr Ser Phe Ile Leu Ala Leu Leu Gln Val
                85                  90                  95

Ser Gly Arg Ala Pro Lys Val Asp Gln Asp Val Ile Asp Arg Ile Lys
            100                 105                 110

Ala Ile Asp Arg Pro Leu His Phe Glu Thr Tyr Val Ser Leu Thr Cys
        115                 120                 125

His Asn Cys Pro Asp Val Val Gln Ala Leu Asn Ile Met Ser Val Leu
    130                 135                 140

Asn Asp Lys Ile Ser His Thr Met Val Glu Gly Met Phe Gln Asp
145                 150                 155                 160

Glu Val Lys Ala Lys Gly Ile Met Ser Val Pro Thr Val Phe Leu Asp
                165                 170                 175

Gly Glu Glu Phe Thr Ser Gly Arg Ala Thr Ile Glu Gln Leu Leu Glu
            180                 185                 190

Gln Val Ala Gly Pro Leu Ser Glu Glu Ala Phe Ala Asp Lys Gly Val
        195                 200                 205

Tyr Asp Val Leu Val Gly Gly Pro Ala Gly Asn Ser Ala Ala
    210                 215                 220

Ile Tyr Ala Ala Arg Lys Gly Leu Lys Thr Gly Leu Leu Ala Glu Thr
225                 230                 235                 240

Phe Gly Gly Gln Val Met Glu Thr Val Gly Ile Glu Asn Met Ile Gly
                245                 250                 255

Thr Leu Tyr Thr Glu Gly Pro Lys Leu Met Ala Glu Val Glu Ala His
            260                 265                 270
```

Thr Lys Ser Tyr Asp Val Asp Ile Ile Lys Ala Gln Leu Ala Thr Ser
        275                 280                 285

Ile Glu Lys Lys Glu Asn Ile Glu Val Thr Leu Ala Asn Gly Ala Val
        290                 295                 300

Leu Gln Ala Lys Thr Ala Ile Leu Ala Leu Gly Ala Lys Trp Arg Asn
305                 310                 315                 320

Ile Asn Val Pro Gly Glu Asp Glu Phe Arg Asn Lys Gly Val Thr Tyr
                325                 330                 335

Cys Pro His Cys Asp Gly Pro Leu Phe Glu Gly Lys Asp Val Ala Val
                340                 345                 350

Ile Gly Gly Gly Asn Ser Gly Leu Glu Ala Ala Leu Asp Leu Ala Gly
            355                 360                 365

Leu Ala Lys His Val Tyr Val Leu Glu Phe Leu Pro Glu Leu Lys Ala
        370                 375                 380

Asp Lys Val Leu Gln Asp Arg Ala Ala Asp Thr Ala Asn Met Thr Ile
385                 390                 395                 400

Ile Lys Asn Val Ala Thr Lys Asp Ile Val Gly Asp His Val Thr
                405                 410                 415

Gly Leu Asn Tyr Thr Glu Arg Asp Ser Gly Glu Asp Lys His Ile Asp
                420                 425                 430

Leu Glu Gly Val Phe Val Gln Ile Gly Leu Val Pro Asn Thr Ala Trp
            435                 440                 445

Leu Lys Asp Ser Gly Val Asn Leu Thr Asp Arg Gly Glu Ile Ile Val
        450                 455                 460

Asp Lys His Gly Ser Thr Asn Ile Pro Gly Ile Phe Ala Ala Gly Asp
465                 470                 475                 480

Cys Thr Asp Ser Ala Tyr Lys Gln Ile Ile Ile Ser Met Gly Ser Gly
                485                 490                 495

Ala Thr Ala Ala Ile Gly Ala Phe Asp Tyr Leu Ile Arg Gln
            500                 505                 510

<210> SEQ ID NO 15
<211> LENGTH: 1938
<212> TYPE: DNA
<213> ORGANISM: Streptococcus agalactiae

<400> SEQUENCE: 15

```
gcggacgacg taacaactga tactgtgacc ttgcacaaga ttgtcatgcc acaagctgca        60
tttgataact ttactgaagg tacaaaaggt aagaatgata gcgattatgt tggtaaacaa       120
attaatgacc ttaaatctta ttttggctca accgatgcta agaaattaa gggtgctttc        180 tttgttttca aaatgaaac tggtacaaaa ttcattactg aaaatggtaa ggaagtcgat        240
actttggaag ctaagatgc tgaaggtggt gctgttcttt cagggttaac aaaagacact        300
ggttttgctt ttaacactgc taagttaaaa ggaacttacc aaatcgttga attgaaagaa       360
aaatcaaact acgataacaa cggttctatc ttggctgatt caaagcagt tccagttaaa        420 atcactctgc cattggtaaa caaccaaggt gttgttaaag atgctcacat ttatccaaag       480
aatactgaaa caaaaccaca agtagataag aactttgcag ataaagatct tgattatact       540
gacaaccgaa agacaaagg tgttgtctca gcgacagttg gtgacaaaaa agaatacata       600
gttggaacaa aaattcttaa aggctcagac tataagaaac tggtttggac tgatagcatg       660
actaaaggtt tgacgttcaa caacaacgtt aaagtaacat tggatggtaa agattttcct      720
gttttaaact acaaactcgt aacagatgac caaggtttcc gtcttgcctt gaatgcaaca      780
```

-continued

| | |
|---|---|
| ggtcttgcag cagtagcagc tgctgcaaaa gacaaagatg ttgaaatcaa gatcacttac | 840 |
| tcagctacgg tgaacggctc cactactgtt gaagttccag aaaccaatga tgttaaattg | 900 |
| gactatggta ataacccaac ggaagaaagt gaaccacaag aaggtactcc agctaaccaa | 960 |
| gaaattaaag tcattaaaga ctgggcagta gatggtacaa ttactgatgt taatgttgca | 1020 |
| gttaaagcta tctttacctt gcaagaaaaa caaacggatg gtacatgggt gaacgttgct | 1080 |
| tcacacgaag caacaaaacc atcacgcttt gaacatactt tcacaggttt ggataatact | 1140 |
| aaaacttacc gcgttgtcga acgtgttagc ggctacactc cagaatatgt atcatttaaa | 1200 |
| aatggtgttg tgactatcaa gaacaacaaa aactcaaatg atccaactcc aatcaaccca | 1260 |
| tcagaaccaa aagtggtgac ttatggacgt aaatttgtga aaacaaatca agctaacact | 1320 |
| gaacgcttgg caggagctac cttccttgtt aagaaagaag gaaaatactt ggcacgtaaa | 1380 |
| gcaggtgcag caactgctga agcaaaggca gctgtaaaaa ctgctaaact agcattggat | 1440 |
| gaagctgtta agcttataa cgacttgact aaagaaaaac aagaaggcca agaaggtaaa | 1500 |
| acagcattgg ctactgttga tcaaaaacaa aaagcttaca tgacgctttt tgttaaagct | 1560 |
| aactactcat atgaatgggt tgcagataaa aaggctgata tgttgttaa attgatctct | 1620 |
| aacgccggtg gtcaatttga attactggt ttggataaag gcacttatag cttggaagaa | 1680 |
| actcaagtac cagcaggtta tgcgacattg tcaggtgatg taaactttga agtaactgcc | 1740 |
| acatcatata gcaaagggc tacaactgac atcgcatatg ataaaggatc tgtaaaaaag | 1800 |
| gatgcccaac aagttcaaaa caaaaagta accatcccac aaacaggtgg tattggtaca | 1860 |
| attcttttca caattattgg tttaagcatt atgcttggag cagtggttgt catgaaaaaa | 1920 |
| cgtcaatcag aggaagct | 1938 |

<210> SEQ ID NO 16
<211> LENGTH: 646
<212> TYPE: PRT
<213> ORGANISM: Streptococcus agalactiae

<400> SEQUENCE: 16

Ala Asp Asp Val Thr Thr Asp Thr Val Thr Leu His Lys Ile Val Met
1               5                   10                  15

Pro Gln Ala Ala Phe Asp Asn Phe Thr Glu Gly Thr Lys Gly Lys Asn
                20                  25                  30

Asp Ser Asp Tyr Val Gly Lys Gln Ile Asn Asp Leu Lys Ser Tyr Phe
            35                  40                  45

Gly Ser Thr Asp Ala Lys Glu Ile Lys Gly Ala Phe Phe Val Phe Lys
        50                  55                  60

Asn Glu Thr Gly Thr Lys Phe Ile Thr Glu Asn Gly Lys Glu Val Asp
65                  70                  75                  80

Thr Leu Glu Ala Lys Asp Ala Glu Gly Gly Ala Val Leu Ser Gly Leu
                85                  90                  95

Thr Lys Asp Thr Gly Phe Ala Phe Asn Thr Ala Lys Leu Lys Gly Thr
            100                 105                 110

Tyr Gln Ile Val Glu Leu Lys Glu Lys Ser Asn Tyr Asp Asn Asn Gly
        115                 120                 125

Ser Ile Leu Ala Asp Ser Lys Ala Val Pro Val Lys Ile Thr Leu Pro
    130                 135                 140

Leu Val Asn Asn Gln Gly Val Val Lys Asp Ala His Ile Tyr Pro Lys
145                 150                 155                 160

Asn Thr Glu Thr Lys Pro Gln Val Asp Lys Asn Phe Ala Asp Lys Asp

-continued

```
                165                 170                 175
Leu Asp Tyr Thr Asp Asn Arg Lys Asp Lys Gly Val Val Ser Ala Thr
                    180                 185                 190

Val Gly Asp Lys Lys Glu Tyr Ile Val Gly Thr Lys Ile Leu Lys Gly
                195                 200                 205

Ser Asp Tyr Lys Lys Leu Val Trp Thr Asp Ser Met Thr Lys Gly Leu
            210                 215                 220

Thr Phe Asn Asn Asn Val Lys Val Thr Leu Asp Gly Lys Asp Phe Pro
225                 230                 235                 240

Val Leu Asn Tyr Lys Leu Val Thr Asp Gln Gly Phe Arg Leu Ala
                    245                 250                 255

Leu Asn Ala Thr Gly Leu Ala Ala Val Ala Ala Ala Lys Asp Lys
                260                 265                 270

Asp Val Glu Ile Lys Ile Thr Tyr Ser Ala Thr Val Asn Gly Ser Thr
                275                 280                 285

Thr Val Glu Val Pro Glu Thr Asn Asp Val Lys Leu Asp Tyr Gly Asn
            290                 295                 300

Asn Pro Thr Glu Glu Ser Glu Pro Gln Glu Gly Thr Pro Ala Asn Gln
305                 310                 315                 320

Glu Ile Lys Val Ile Lys Asp Trp Ala Val Asp Gly Thr Ile Thr Asp
                    325                 330                 335

Val Asn Val Ala Val Lys Ala Ile Phe Thr Leu Gln Glu Lys Gln Thr
                340                 345                 350

Asp Gly Thr Trp Val Asn Val Ala Ser His Glu Ala Thr Lys Pro Ser
            355                 360                 365

Arg Phe Glu His Thr Phe Thr Gly Leu Asp Asn Thr Lys Thr Tyr Arg
            370                 375                 380

Val Val Glu Arg Val Ser Gly Tyr Thr Pro Glu Tyr Val Ser Phe Lys
385                 390                 395                 400

Asn Gly Val Val Thr Ile Lys Asn Asn Lys Asn Ser Asn Asp Pro Thr
                    405                 410                 415

Pro Ile Asn Pro Ser Glu Pro Lys Val Val Thr Tyr Gly Arg Lys Phe
                420                 425                 430

Val Lys Thr Asn Gln Ala Asn Thr Glu Arg Leu Ala Gly Ala Thr Phe
            435                 440                 445

Leu Val Lys Lys Glu Gly Lys Tyr Leu Ala Arg Lys Ala Gly Ala Ala
            450                 455                 460

Thr Ala Glu Ala Lys Ala Ala Val Lys Thr Ala Lys Leu Ala Leu Asp
465                 470                 475                 480

Glu Ala Val Lys Ala Tyr Asn Asp Leu Thr Lys Glu Lys Gln Glu Gly
                    485                 490                 495

Gln Glu Gly Lys Thr Ala Leu Ala Thr Val Asp Gln Lys Gln Lys Ala
                500                 505                 510

Tyr Asn Asp Ala Phe Val Lys Ala Asn Tyr Ser Tyr Glu Trp Val Ala
            515                 520                 525

Asp Lys Lys Ala Asp Asn Val Val Lys Leu Ile Ser Asn Ala Gly Gly
            530                 535                 540

Gln Phe Glu Ile Thr Gly Leu Asp Lys Gly Thr Tyr Ser Leu Glu Glu
545                 550                 555                 560

Thr Gln Val Pro Ala Gly Tyr Ala Thr Leu Ser Gly Asp Val Asn Phe
                    565                 570                 575

Glu Val Thr Ala Thr Ser Tyr Ser Lys Gly Ala Thr Thr Asp Ile Ala
                580                 585                 590
```

```
Tyr Asp Lys Gly Ser Val Lys Asp Ala Gln Gln Val Gln Asn Lys
        595                 600                 605

Lys Val Thr Ile Pro Gln Thr Gly Gly Ile Gly Thr Ile Leu Phe Thr
    610                 615                 620

Ile Ile Gly Leu Ser Ile Met Leu Gly Ala Val Val Met Lys Lys
625                 630                 635                 640

Arg Gln Ser Glu Glu Ala
                645

<210> SEQ ID NO 17
<211> LENGTH: 434
<212> TYPE: PRT
<213> ORGANISM: Streptococcus agalactiae

<400> SEQUENCE: 17

Met Ser Tyr Tyr His His His His His Leu Glu Ser Thr Ser Leu
1               5                   10                  15

Tyr Lys Lys Ala Gly Leu Ala Ser Lys Thr Thr Ile Lys Leu Trp Val
            20                  25                  30

Pro Thr Asp Ser Lys Ala Ser Tyr Lys Ala Ile Val Lys Lys Phe Glu
        35                  40                  45

Lys Glu Asn Lys Gly Val Thr Val Lys Met Ile Glu Ser Asn Asp Ser
50                  55                  60

Lys Ala Gln Glu Asn Val Lys Lys Asp Pro Ser Lys Ala Ala Asp Val
65                  70                  75                  80

Phe Ser Leu Pro His Asp Gln Leu Gly Gln Leu Val Glu Ser Gly Val
            85                  90                  95

Ile Gln Glu Ile Pro Glu Gln Tyr Ser Lys Glu Ile Ala Lys Asn Asp
        100                 105                 110

Thr Lys Gln Ser Leu Thr Gly Ala Gln Tyr Lys Gly Lys Thr Tyr Ala
    115                 120                 125

Phe Pro Phe Gly Ile Glu Ser Gln Val Leu Tyr Tyr Asn Lys Thr Lys
    130                 135                 140

Leu Thr Ala Asp Asp Val Lys Ser Tyr Glu Thr Ile Thr Ser Lys Gly
145                 150                 155                 160

Lys Phe Gly Gln Gln Leu Lys Ala Ala Asn Ser Tyr Val Thr Gly Pro
            165                 170                 175

Leu Phe Leu Ser Val Gly Asp Thr Leu Phe Gly Lys Ser Gly Glu Asp
        180                 185                 190

Ala Lys Gly Thr Asn Trp Gly Asn Glu Ala Gly Val Ser Val Leu Lys
    195                 200                 205

Trp Ile Ala Asp Gln Lys Lys Asn Asp Gly Phe Val Asn Leu Thr Ala
    210                 215                 220

Glu Asn Thr Met Ser Lys Phe Gly Asp Gly Ser Val His Ala Phe Glu
225                 230                 235                 240

Ser Gly Pro Trp Asp Tyr Asp Ala Ala Lys Lys Ala Val Gly Glu Asp
            245                 250                 255

Lys Ile Gly Val Ala Val Tyr Pro Thr Met Lys Ile Gly Asp Lys Glu
        260                 265                 270

Val Gln Gln Lys Ala Phe Leu Gly Val Lys Leu Tyr Ala Val Asn Gln
    275                 280                 285

Ala Pro Ala Gly Ser Asn Thr Lys Arg Ile Ser Ala Ser Tyr Lys Leu
    290                 295                 300

Ala Ala Tyr Leu Thr Asn Ala Glu Ser Gln Lys Ile Gln Phe Glu Lys
```

```
305                 310                 315                 320
Arg His Ile Val Pro Ala Asn Ser Ser Ile Gln Ser Ser Asp Ser Val
                325                 330                 335

Gln Lys Asp Glu Leu Ala Lys Ala Val Ile Glu Met Gly Ser Ser Asp
                340                 345                 350

Lys Tyr Thr Thr Val Met Pro Lys Leu Ser Gln Met Ser Thr Phe Trp
                355                 360                 365

Thr Glu Ser Ala Ala Ile Leu Ser Asp Thr Tyr Ser Gly Lys Ile Lys
        370                 375                 380

Ser Ser Asp Tyr Leu Lys Arg Leu Lys Gln Phe Asp Lys Asp Ile Ala
385                 390                 395                 400

Lys Thr Lys Tyr Pro Ala Phe Leu Tyr Lys Val Val Asp Ser Arg Leu
                405                 410                 415

Leu Thr Lys Pro Glu Arg Lys Leu Ser Trp Leu Leu Pro Pro Leu Ser
                420                 425                 430

Asn Asn

<210> SEQ ID NO 18
<211> LENGTH: 539
<212> TYPE: PRT
<213> ORGANISM: Streptococcus agalactiae

<400> SEQUENCE: 18

Met Ser Tyr Tyr His His His His His His Leu Glu Ser Thr Ser Leu
1               5                   10                  15

Tyr Lys Lys Ala Gly Leu Ala Glu Thr Ile Asn Pro Glu Thr Ser Leu
                20                  25                  30

Thr Met Ala Thr Ala Ser Thr Glu Ser Ser Ser Glu Ala Glu Lys Gln
            35                  40                  45

Glu Lys Thr Gln Pro Thr Asp Ser Glu Thr Ala Ser Pro Ser Ala Glu
        50                  55                  60

Gly Ser Ile Ser Thr Glu Lys Thr Glu Ile Gly Thr Thr Glu Thr Ser
65                  70                  75                  80

Ser Ser Asn Glu Ser Ser Ser Ser Ser His Gln Ser Ser Ser Asn
                85                  90                  95

Glu Asp Ala Lys Thr Ser Asp Ser Ala Ser Thr Ala Ser Thr Pro Ser
                100                 105                 110

Thr Asn Thr Thr Asn Ser Ser Gln Ala Asp Ser Lys Pro Gly Gln Ser
            115                 120                 125

Thr Lys Thr Glu Leu Lys Pro Glu Pro Thr Leu Pro Leu Val Glu Pro
        130                 135                 140

Lys Ile Thr Pro Ala Pro Ser Gln Ile Glu Ser Val Gln Thr Asn Gln
145                 150                 155                 160

Asn Ala Ser Val Pro Ala Leu Ser Phe Asp Asp Asn Leu Leu Ser Thr
                165                 170                 175

Pro Ile Ser Pro Val Thr Ala Thr Pro Phe Tyr Val Glu His Trp Ser
                180                 185                 190

Gly Gln Asp Ala Tyr Ser His Tyr Leu Leu Ser His Arg Tyr Gly Ile
            195                 200                 205

Lys Ala Glu Gln Leu Asp Gly Tyr Leu Lys Ser Leu Gly Ile Gln Tyr
        210                 215                 220

Asp Ser Asn Arg Ile Asn Gly Ala Lys Leu Leu Gln Trp Glu Lys Asp
225                 230                 235                 240

Ser Gly Leu Asp Val Arg Ala Ile Val Ala Ile Ala Val Leu Glu Ser
```

```
                245                 250                 255
Ser Leu Gly Thr Gln Gly Val Ala Lys Met Pro Gly Ala Asn Met Phe
            260                 265                 270

Gly Tyr Gly Ala Phe Asp His Asp Ser Ser His Ala Ser Ala Tyr Asn
            275                 280                 285

Asp Glu Glu Ala Ile Met Leu Leu Thr Lys Asn Thr Ile Ile Lys Asn
        290                 295                 300

Asn Asn Ser Ser Phe Glu Ile Gln Asp Leu Lys Ala Gln Lys Leu Ser
305                 310                 315                 320

Ser Gly Gln Leu Asn Thr Val Thr Glu Gly Val Tyr Tyr Thr Asp
            325                 330                 335

Asn Ser Gly Thr Gly Lys Arg Arg Ala Gln Ile Met Glu Asp Leu Asp
            340                 345                 350

Arg Trp Ile Asp Gln His Gly Gly Thr Pro Glu Ile Pro Ala Ala Leu
            355                 360                 365

Lys Ala Leu Ser Thr Ala Ser Leu Ala Asp Leu Pro Ser Gly Phe Ser
            370                 375                 380

Leu Ser Thr Ala Val Asn Thr Ala Ser Tyr Ile Ala Ser Thr Tyr Pro
385                 390                 395                 400

Trp Gly Glu Cys Thr Trp Tyr Val Phe Asn Arg Ala Lys Glu Leu Gly
                405                 410                 415

Tyr Thr Phe Asp Pro Phe Met Gly Asn Gly Gly Asp Trp Gln His Lys
            420                 425                 430

Ala Gly Phe Glu Thr Thr His Ser Pro Lys Val Gly Tyr Ala Val Ser
            435                 440                 445

Phe Ser Pro Gly Gln Ala Gly Ala Asp Gly Thr Tyr Gly His Val Ala
        450                 455                 460

Ile Val Glu Glu Val Lys Lys Asp Gly Ser Val Leu Ile Ser Glu Ser
465                 470                 475                 480

Asn Ala Met Gly Arg Gly Ile Val Ser Tyr Arg Thr Phe Ser Ser Ala
            485                 490                 495

Gln Ala Ala Gln Leu Thr Tyr Val Ile Gly His Lys Tyr Pro Ala Phe
            500                 505                 510

Leu Tyr Lys Val Val Asp Ser Arg Leu Leu Thr Lys Pro Glu Arg Lys
            515                 520                 525

Leu Ser Trp Leu Leu Pro Pro Leu Ser Asn Asn
            530                 535

<210> SEQ ID NO 19
<211> LENGTH: 463
<212> TYPE: PRT
<213> ORGANISM: Streptococcus agalactiae

<400> SEQUENCE: 19

Met Ser Tyr Tyr His His His His His His Leu Glu Ser Thr Ser Leu
1               5                   10                  15

Tyr Lys Lys Ala Gly Leu Ala Gln Glu Thr Asp Thr Thr Trp Thr Ala
            20                  25                  30

Arg Thr Val Ser Glu Val Lys Ala Asp Leu Val Lys Gln Asp Asn Lys
        35                  40                  45

Ser Ser Tyr Thr Val Lys Tyr Gly Asp Thr Leu Ser Val Ile Ser Glu
    50                  55                  60

Ala Met Ser Ile Asp Met Asn Val Leu Ala Lys Ile Asn Asn Ile Ala
65                  70                  75                  80
```

-continued

```
Asp Ile Asn Leu Ile Tyr Pro Glu Thr Thr Leu Thr Val Thr Tyr Asp
             85                  90                  95
Gln Lys Ser His Thr Ala Thr Ser Met Lys Ile Glu Thr Pro Ala Thr
         100                 105                 110
Asn Ala Ala Gly Gln Thr Thr Ala Thr Val Asp Leu Lys Thr Asn Gln
     115                 120                 125
Val Ser Val Ala Asp Gln Lys Val Ser Leu Asn Thr Ile Ser Glu Gly
 130                 135                 140
Met Thr Pro Glu Ala Ala Thr Thr Ile Val Ser Pro Met Lys Thr Tyr
145                 150                 155                 160
Ser Ser Ala Pro Ala Leu Lys Ser Lys Glu Val Leu Ala Gln Glu Gln
                 165                 170                 175
Ala Val Ser Gln Ala Ala Asn Glu Gln Val Ser Pro Ala Pro Val
             180                 185                 190
Lys Ser Ile Thr Ser Glu Val Pro Ala Ala Lys Glu Val Lys Pro
         195                 200                 205
Thr Gln Thr Ser Val Ser Gln Ser Thr Thr Val Ser Pro Ala Ser Val
     210                 215                 220
Ala Ala Glu Thr Pro Ala Pro Val Ala Lys Val Ala Pro Val Arg Thr
225                 230                 235                 240
Val Ala Ala Pro Arg Val Ala Ser Val Lys Val Val Thr Pro Lys Val
                 245                 250                 255
Glu Thr Gly Ala Ser Pro Glu His Val Ser Ala Pro Ala Val Pro Val
             260                 265                 270
Thr Thr Thr Ser Pro Ala Thr Asp Ser Lys Leu Gln Ala Thr Glu Val
         275                 280                 285
Lys Ser Val Pro Val Ala Gln Lys Ala Pro Thr Ala Thr Pro Val Ala
     290                 295                 300
Gln Pro Ala Ser Thr Thr Asn Ala Val Ala Ala His Pro Glu Asn Ala
305                 310                 315                 320
Gly Leu Gln Pro His Val Ala Ala Tyr Lys Glu Lys Val Ala Ser Thr
                 325                 330                 335
Tyr Gly Val Asn Glu Phe Ser Thr Tyr Arg Ala Gly Asp Pro Gly Asp
             340                 345                 350
His Gly Lys Gly Leu Ala Val Asp Phe Ile Val Gly Thr Asn Gln Ala
         355                 360                 365
Leu Gly Asn Lys Val Ala Gln Tyr Ser Thr Gln Asn Met Ala Ala Asn
     370                 375                 380
Asn Ile Ser Tyr Val Ile Trp Gln Gln Lys Phe Tyr Ser Asn Thr Asn
385                 390                 395                 400
Ser Ile Tyr Gly Pro Ala Asn Thr Trp Asn Ala Met Pro Asp Arg Gly
                 405                 410                 415
Gly Val Thr Ala Asn His Tyr Asp His Val His Val Ser Phe Asn Lys
             420                 425                 430
Tyr Pro Ala Phe Leu Tyr Lys Val Val Asp Ser Arg Leu Leu Thr Lys
         435                 440                 445
Pro Glu Arg Lys Leu Ser Trp Leu Leu Pro Pro Leu Ser Asn Asn
     450                 455                 460

<210> SEQ ID NO 20
<211> LENGTH: 280
<212> TYPE: PRT
<213> ORGANISM: Streptococcus agalactiae

<400> SEQUENCE: 20
```

```
Met Ser Tyr Tyr His His His His His Leu Glu Ser Thr Ser Leu
1               5                   10                  15

Tyr Lys Lys Ala Gly Leu Ala Asp Gln Val Thr Thr Pro Gln Val Val
                20                  25                  30

Asn His Val Asn Ser Asn Asn Gln Ala Gln Gln Met Ala Gln Lys Leu
            35                  40                  45

Asp Gln Asp Ser Ile Gln Leu Arg Asn Ile Lys Asp Asn Val Gln Gly
        50                  55                  60

Thr Asp Tyr Glu Lys Thr Val Asn Glu Ala Ile Thr Ser Val Glu Lys
65                  70                  75                  80

Leu Lys Thr Ser Leu Arg Ala Asn Pro Glu Thr Val Tyr Asp Leu Asn
                85                  90                  95

Ser Ile Gly Ser Arg Val Glu Ala Leu Thr Asp Val Ile Glu Ala Ile
            100                 105                 110

Thr Phe Ser Thr Gln His Leu Ala Asn Lys Val Ser Gln Ala Asn Ile
        115                 120                 125

Asp Met Gly Phe Gly Ile Thr Lys Leu Val Ile Arg Ile Leu Asp Pro
    130                 135                 140

Phe Ala Ser Val Asp Ser Ile Lys Ala Gln Val Asn Asp Val Lys Ala
145                 150                 155                 160

Leu Glu Gln Lys Val Leu Thr Tyr Pro Asp Leu Lys Pro Thr Asp Arg
                165                 170                 175

Ala Thr Ile Tyr Thr Lys Ser Lys Leu Asp Lys Glu Ile Trp Asn Thr
            180                 185                 190

Arg Phe Thr Arg Asp Lys Lys Val Leu Asn Val Lys Glu Phe Lys Val
        195                 200                 205

Tyr Asn Thr Leu Asn Lys Ala Ile Thr His Ala Val Gly Val Gln Leu
    210                 215                 220

Asn Pro Asn Val Thr Val Gln Gln Val Asp Gln Glu Ile Val Thr Leu
225                 230                 235                 240

Gln Ala Ala Leu Gln Thr Ala Leu Lys Tyr Pro Ala Phe Leu Tyr Lys
                245                 250                 255

Val Val Asp Ser Arg Leu Leu Thr Lys Pro Glu Arg Lys Leu Ser Trp
            260                 265                 270

Leu Leu Pro Pro Leu Ser Asn Asn
        275                 280

<210> SEQ ID NO 21
<211> LENGTH: 553
<212> TYPE: PRT
<213> ORGANISM: Streptococcus agalactiae

<400> SEQUENCE: 21

Met Ser Tyr Tyr His His His His His Leu Glu Ser Thr Ser Leu
1               5                   10                  15

Tyr Lys Lys Ala Gly Leu Gly Glu Ser Thr Val Pro Glu Asn Gly Ala
                20                  25                  30

Lys Gly Lys Leu Val Val Lys Lys Thr Asp Asp Gln Asn Lys Pro Leu
            35                  40                  45

Ser Lys Ala Thr Phe Val Leu Lys Thr Thr Ala His Pro Glu Ser Lys
        50                  55                  60

Ile Glu Lys Val Thr Ala Glu Leu Thr Gly Glu Ala Thr Phe Asp Asn
65                  70                  75                  80

Leu Ile Pro Gly Gly Tyr Thr Leu Ser Glu Glu Thr Ala Pro Glu Gly
```

```
                        85                  90                  95
Tyr Lys Lys Thr Asn Gln Thr Trp Gln Val Lys Val Glu Ser Asn Gly
                    100                 105                 110

Lys Thr Thr Ile Gln Asn Ser Gly Asp Lys Asn Ser Thr Ile Gly Gln
                115                 120                 125

Asn His Glu Glu Leu Asp Lys Gln Tyr Pro Pro Thr Gly Ile Tyr Glu
            130                 135                 140

Asp Thr Lys Glu Ser Tyr Lys Leu Glu His Val Lys Gly Ser Val Pro
145                 150                 155                 160

Asn Gly Lys Ser Glu Ala Lys Ala Val Asn Pro Tyr Ser Ser Glu Gly
                165                 170                 175

Glu His Ile Arg Glu Ile Pro Glu Gly Thr Leu Ser Lys Arg Ile Ser
            180                 185                 190

Glu Val Gly Asp Leu Ala His Asn Lys Tyr Lys Ile Glu Leu Thr Val
        195                 200                 205

Ser Gly Lys Thr Ile Val Lys Pro Val Asp Lys Gln Lys Pro Leu Asp
    210                 215                 220

Val Val Phe Val Leu Asp Asn Ser Asn Ser Met Asn Asn Asp Gly Pro
225                 230                 235                 240

Asn Phe Gln Arg His Asn Lys Ala Lys Lys Ala Ala Glu Ala Leu Gly
                245                 250                 255

Thr Ala Val Lys Asp Ile Leu Gly Ala Asn Ser Asp Asn Arg Val Ala
            260                 265                 270

Leu Val Thr Tyr Gly Ser Asp Ile Phe Asp Gly Arg Ser Val Asp Val
        275                 280                 285

Val Lys Gly Phe Lys Glu Asp Asp Lys Tyr Tyr Gly Leu Gln Thr Lys
    290                 295                 300

Phe Thr Ile Gln Thr Glu Asn Tyr Ser His Lys Gln Leu Thr Asn Asn
305                 310                 315                 320

Ala Glu Glu Ile Ile Lys Arg Ile Pro Thr Glu Ala Pro Arg Ala Lys
                325                 330                 335

Trp Gly Ser Thr Thr Asn Gly Leu Thr Pro Glu Gln Gln Lys Gln Tyr
            340                 345                 350

Tyr Leu Ser Lys Val Gly Glu Thr Phe Thr Met Lys Ala Phe Met Glu
        355                 360                 365

Ala Asp Asp Ile Leu Ser Gln Val Asp Arg Asn Ser Gln Lys Ile Ile
    370                 375                 380

Val His Ile Thr Asp Gly Val Pro Thr Arg Ser Tyr Ala Ile Asn Asn
385                 390                 395                 400

Phe Lys Leu Gly Ala Ser Tyr Glu Ser Gln Phe Glu Gln Met Lys Lys
                405                 410                 415

Asn Gly Tyr Leu Asn Lys Ser Asn Phe Leu Leu Thr Asp Lys Pro Glu
            420                 425                 430

Asp Ile Lys Gly Asn Gly Glu Ser Tyr Phe Leu Phe Pro Leu Asp Ser
        435                 440                 445

Tyr Gln Thr Gln Ile Ile Ser Gly Asn Leu Gln Lys Leu His Tyr Leu
    450                 455                 460

Asp Leu Asn Leu Asn Tyr Pro Lys Gly Thr Ile Tyr Arg Asn Gly Pro
465                 470                 475                 480

Val Arg Glu His Gly Thr Pro Thr Lys Leu Tyr Ile Asn Ser Leu Lys
                485                 490                 495

Gln Lys Asn Tyr Asp Ile Phe Asn Phe Gly Ile Asp Ile Ser Ala Phe
            500                 505                 510
```

Arg Gln Val Tyr Asn Glu Asp Tyr Lys Lys Tyr Pro Ala Phe Leu Tyr
            515                 520                 525

Lys Val Val Asp Ser Arg Leu Leu Thr Lys Pro Glu Arg Lys Leu Ser
            530                 535                 540

Trp Leu Leu Pro Pro Leu Ser Asn Asn
545                 550

<210> SEQ ID NO 22
<211> LENGTH: 594
<212> TYPE: PRT
<213> ORGANISM: Streptococcus agalactiae

<400> SEQUENCE: 22

Met Ser Tyr Tyr His His His His His His Leu Glu Ser Thr Ser Leu
1               5                   10                  15

Tyr Lys Lys Ala Gly Leu Ala Asp Ser Asn Lys Gln Asn Thr Ala Asn
            20                  25                  30

Thr Glu Thr Thr Thr Thr Asn Glu Gln Pro Lys Pro Glu Ser Ser Glu
        35                  40                  45

Leu Thr Thr Glu Lys Ala Gly Gln Lys Met Asp Asp Met Leu Asn Ser
50                  55                  60

Asn Asp Met Ile Lys Leu Ala Pro Lys Glu Met Pro Leu Glu Ser Ala
65                  70                  75                  80

Glu Lys Glu Glu Lys Ser Glu Asp Asn Lys Lys Ser Glu Glu Asp
                85                  90                  95

His Thr Glu Glu Ile Asn Asp Lys Ile Tyr Ser Leu Asn Tyr Asn Glu
            100                 105                 110

Leu Glu Val Leu Ala Lys Asn Gly Glu Thr Ile Glu Asn Phe Val Pro
        115                 120                 125

Lys Glu Gly Val Lys Lys Ala Asp Lys Phe Ile Val Ile Glu Arg Lys
130                 135                 140

Lys Lys Asn Ile Asn Thr Thr Pro Val Asp Ile Ser Ile Ile Asp Ser
145                 150                 155                 160

Val Thr Asp Arg Thr Tyr Pro Ala Ala Leu Gln Leu Ala Asn Lys Gly
            165                 170                 175

Phe Thr Glu Asn Lys Pro Asp Ala Val Val Thr Lys Arg Asn Pro Gln
        180                 185                 190

Lys Ile His Ile Asp Leu Pro Gly Met Gly Asp Lys Ala Thr Val Glu
    195                 200                 205

Val Asn Asp Pro Thr Tyr Ala Asn Val Ser Thr Ala Ile Asp Asn Leu
210                 215                 220

Val Asn Gln Trp His Asp Asn Tyr Ser Gly Gly Asn Thr Leu Pro Ala
225                 230                 235                 240

Arg Thr Gln Tyr Thr Glu Ser Met Val Tyr Ser Lys Ser Gln Ile Glu
            245                 250                 255

Ala Ala Leu Asn Val Asn Ser Lys Ile Leu Asp Gly Thr Leu Gly Ile
        260                 265                 270

Asp Phe Lys Ser Ile Ser Lys Gly Glu Lys Lys Val Met Ile Ala Ala
    275                 280                 285

Tyr Lys Gln Ile Phe Tyr Thr Val Ser Ala Asn Leu Pro Asn Asn Pro
    290                 295                 300

Ala Asp Val Phe Asp Lys Ser Val Thr Phe Lys Glu Leu Gln Arg Lys
305                 310                 315                 320

Gly Val Ser Asn Glu Ala Pro Pro Leu Phe Val Ser Asn Val Ala Tyr

```
                    325                 330                 335
Gly Arg Thr Val Phe Val Lys Leu Glu Thr Ser Ser Lys Ser Asn Asp
            340                 345                 350

Val Glu Ala Ala Phe Ser Ala Ala Leu Lys Gly Thr Asp Val Lys Thr
        355                 360                 365

Asn Gly Lys Tyr Ser Asp Ile Leu Glu Asn Ser Ser Phe Thr Ala Val
    370                 375                 380

Val Leu Gly Gly Asp Ala Ala Glu His Asn Lys Val Val Thr Lys Asp
385                 390                 395                 400

Phe Asp Val Ile Arg Asn Val Ile Lys Asp Asn Ala Thr Phe Ser Arg
                405                 410                 415

Lys Asn Pro Ala Tyr Pro Ile Ser Tyr Thr Ser Val Phe Leu Lys Asn
            420                 425                 430

Asn Lys Ile Ala Gly Val Asn Asn Arg Ser Glu Tyr Val Glu Thr Thr
        435                 440                 445

Ser Thr Glu Tyr Thr Ser Gly Lys Ile Asn Leu Ser His Gln Gly Ala
    450                 455                 460

Tyr Val Ala Gln Tyr Glu Ile Leu Trp Asp Glu Ile Asn Tyr Asp Asp
465                 470                 475                 480

Lys Gly Lys Glu Val Ile Thr Lys Arg Trp Asp Asn Asn Trp Tyr
                485                 490                 495

Ser Lys Thr Ser Pro Phe Ser Thr Val Ile Pro Leu Gly Ala Asn Ser
            500                 505                 510

Arg Asn Ile Arg Ile Met Ala Arg Glu Cys Thr Gly Leu Ala Trp Glu
        515                 520                 525

Trp Trp Arg Lys Val Ile Asp Glu Arg Asp Val Lys Leu Ser Lys Glu
    530                 535                 540

Ile Asn Val Asn Ile Ser Gly Ser Thr Leu Ser Pro Tyr Gly Ser Ile
545                 550                 555                 560

Thr Tyr Lys Tyr Pro Ala Phe Leu Tyr Lys Val Val Asp Ser Arg Leu
                565                 570                 575

Leu Thr Lys Pro Glu Arg Lys Leu Ser Trp Leu Leu Pro Pro Leu Ser
            580                 585                 590

Asn Asn

<210> SEQ ID NO 23
<211> LENGTH: 563
<212> TYPE: PRT
<213> ORGANISM: Streptococcus agalactiae

<400> SEQUENCE: 23

Met Ser Tyr Tyr His His His His His His Leu Glu Ser Thr Ser Leu
1               5                   10                  15

Tyr Lys Lys Ala Gly Leu Met Ala Leu Ser Pro Asp Ile Lys Glu Gln
            20                  25                  30

Leu Ala Gln Tyr Leu Thr Leu Leu Glu Ser Asp Leu Val Leu Gln Ala
        35                  40                  45

Tyr Leu Gly Asp Asp Glu Gln Ser Gln Lys Val Lys Asp Phe Val Glu
    50                  55                  60

Glu Ile Ala Ala Met Ser Asp Arg Ile Ser Val Glu Glu Thr Val Leu
65                  70                  75                  80

Asp Arg Lys Pro Ser Phe Lys Val Ala Lys Lys Gly Gln Asp Ser Gly
                85                  90                  95

Val Ala Phe Ala Gly Leu Pro Leu Gly His Glu Phe Thr Ser Phe Ile
```

-continued

```
                100                 105                 110
Leu Ala Leu Leu Gln Val Ser Gly Arg Ala Pro Lys Val Asp Gln Asp
            115                 120                 125
Val Ile Asp Arg Ile Lys Ala Ile Asp Arg Pro Leu His Phe Glu Thr
        130                 135                 140
Tyr Val Ser Leu Thr Cys His Asn Cys Pro Asp Val Val Gln Ala Leu
145                 150                 155                 160
Asn Ile Met Ser Val Leu Asn Asp Lys Ile Ser His Thr Met Val Glu
                165                 170                 175
Gly Gly Met Phe Gln Asp Glu Val Lys Ala Lys Gly Ile Met Ser Val
            180                 185                 190
Pro Thr Val Phe Leu Asp Gly Glu Glu Phe Thr Ser Gly Arg Ala Thr
        195                 200                 205
Ile Glu Gln Leu Leu Glu Gln Val Ala Gly Pro Leu Ser Glu Glu Ala
    210                 215                 220
Phe Ala Asp Lys Gly Val Tyr Asp Val Leu Val Val Gly Gly Gly Pro
225                 230                 235                 240
Ala Gly Asn Ser Ala Ala Ile Tyr Ala Ala Arg Lys Gly Leu Lys Thr
                245                 250                 255
Gly Leu Leu Ala Glu Thr Phe Gly Gly Gln Val Met Glu Thr Val Gly
            260                 265                 270
Ile Glu Asn Met Ile Gly Thr Leu Tyr Thr Glu Gly Pro Lys Leu Met
        275                 280                 285
Ala Glu Val Glu Ala His Thr Lys Ser Tyr Asp Val Asp Ile Ile Lys
    290                 295                 300
Ala Gln Leu Ala Thr Ser Ile Glu Lys Lys Glu Asn Ile Glu Val Thr
305                 310                 315                 320
Leu Ala Asn Gly Ala Val Leu Gln Ala Lys Thr Ala Ile Leu Ala Leu
                325                 330                 335
Gly Ala Lys Trp Arg Asn Ile Asn Val Pro Gly Glu Asp Glu Phe Arg
            340                 345                 350
Asn Lys Gly Val Thr Tyr Cys Pro His Cys Asp Gly Pro Leu Phe Glu
        355                 360                 365
Gly Lys Asp Val Ala Val Ile Gly Gly Gly Asn Ser Gly Leu Glu Ala
    370                 375                 380
Ala Leu Asp Leu Ala Gly Leu Ala Lys His Val Tyr Val Leu Glu Phe
385                 390                 395                 400
Leu Pro Glu Leu Lys Ala Asp Lys Val Leu Gln Asp Arg Ala Ala Asp
                405                 410                 415
Thr Ala Asn Met Thr Ile Ile Lys Asn Val Ala Thr Lys Asp Ile Val
            420                 425                 430
Gly Asp Asp His Val Thr Gly Leu Asn Tyr Thr Glu Arg Asp Ser Gly
        435                 440                 445
Glu Asp Lys His Ile Asp Leu Glu Gly Val Phe Val Gln Ile Gly Leu
    450                 455                 460
Val Pro Asn Thr Ala Trp Leu Lys Asp Ser Gly Val Asn Leu Thr Asp
465                 470                 475                 480
Arg Gly Glu Ile Ile Val Asp Lys His Gly Ser Thr Asn Ile Pro Gly
                485                 490                 495
Ile Phe Ala Ala Gly Asp Cys Thr Asp Ser Tyr Lys Gln Ile Ile
            500                 505                 510
Ile Ser Met Gly Ser Gly Ala Thr Ala Ala Ile Gly Ala Phe Asp Tyr
        515                 520                 525
```

-continued

```
Leu Ile Arg Gln Tyr Pro Ala Phe Leu Tyr Lys Val Val Asp Ser Arg
            530                 535                 540
Leu Leu Thr Lys Pro Glu Arg Lys Leu Ser Trp Leu Leu Pro Pro Leu
545                 550                 555                 560
Ser Asn Asn

<210> SEQ ID NO 24
<211> LENGTH: 699
<212> TYPE: PRT
<213> ORGANISM: Streptococcus agalactiae

<400> SEQUENCE: 24

Met Ser Tyr Tyr His His His His His His Leu Glu Ser Thr Ser Leu
1               5                   10                  15
Tyr Lys Lys Ala Gly Leu Ala Asp Asp Val Thr Thr Asp Thr Val Thr
            20                  25                  30
Leu His Lys Ile Val Met Pro Gln Ala Ala Phe Asp Asn Phe Thr Glu
        35                  40                  45
Gly Thr Lys Gly Lys Asn Asp Ser Asp Tyr Val Gly Lys Gln Ile Asn
    50                  55                  60
Asp Leu Lys Ser Tyr Phe Gly Ser Thr Asp Ala Lys Glu Ile Lys Gly
65                  70                  75                  80
Ala Phe Phe Val Phe Lys Asn Glu Thr Gly Thr Lys Phe Ile Thr Glu
                85                  90                  95
Asn Gly Lys Glu Val Asp Thr Leu Glu Ala Lys Asp Ala Glu Gly Gly
            100                 105                 110
Ala Val Leu Ser Gly Leu Thr Lys Asp Thr Gly Phe Ala Phe Asn Thr
        115                 120                 125
Ala Lys Leu Lys Gly Thr Tyr Gln Ile Val Glu Leu Lys Glu Lys Ser
    130                 135                 140
Asn Tyr Asp Asn Asn Gly Ser Ile Leu Ala Asp Ser Lys Ala Val Pro
145                 150                 155                 160
Val Lys Ile Thr Leu Pro Leu Val Asn Asn Gln Gly Val Val Lys Asp
                165                 170                 175
Ala His Ile Tyr Pro Lys Asn Thr Glu Thr Lys Pro Gln Val Asp Lys
            180                 185                 190
Asn Phe Ala Asp Lys Asp Leu Asp Tyr Thr Asp Asn Arg Lys Asp Lys
        195                 200                 205
Gly Val Val Ser Ala Thr Val Gly Asp Lys Lys Glu Tyr Ile Val Gly
    210                 215                 220
Thr Lys Ile Leu Lys Gly Ser Asp Tyr Lys Lys Leu Val Trp Thr Asp
225                 230                 235                 240
Ser Met Thr Lys Gly Leu Thr Phe Asn Asn Asn Val Lys Val Thr Leu
                245                 250                 255
Asp Gly Lys Asp Phe Pro Val Leu Asn Tyr Lys Leu Val Thr Asp Asp
            260                 265                 270
Gln Gly Phe Arg Leu Ala Leu Asn Ala Thr Gly Leu Ala Ala Val Ala
        275                 280                 285
Ala Ala Ala Lys Asp Lys Asp Val Glu Ile Lys Ile Thr Tyr Ser Ala
    290                 295                 300
Thr Val Asn Gly Ser Thr Thr Val Glu Val Pro Glu Thr Asn Asp Val
305                 310                 315                 320
Lys Leu Asp Tyr Gly Asn Asn Pro Thr Glu Glu Ser Glu Pro Gln Glu
                325                 330                 335
```

-continued

```
Gly Thr Pro Ala Asn Gln Glu Ile Lys Val Ile Lys Asp Trp Ala Val
            340                 345                 350

Asp Gly Thr Ile Thr Asp Val Asn Val Ala Val Lys Ala Ile Phe Thr
            355                 360                 365

Leu Gln Glu Lys Gln Thr Asp Gly Thr Trp Val Asn Val Ala Ser His
    370                 375                 380

Glu Ala Thr Lys Pro Ser Arg Phe Glu His Thr Phe Thr Gly Leu Asp
385                 390                 395                 400

Asn Thr Lys Thr Tyr Arg Val Val Glu Arg Val Ser Gly Tyr Thr Pro
                405                 410                 415

Glu Tyr Val Ser Phe Lys Asn Gly Val Val Thr Ile Lys Asn Asn Lys
            420                 425                 430

Asn Ser Asn Asp Pro Thr Pro Ile Asn Pro Ser Glu Pro Lys Val Val
            435                 440                 445

Thr Tyr Gly Arg Lys Phe Val Lys Thr Asn Gln Ala Asn Thr Glu Arg
    450                 455                 460

Leu Ala Gly Ala Thr Phe Leu Val Lys Lys Glu Gly Lys Tyr Leu Ala
465                 470                 475                 480

Arg Lys Ala Gly Ala Ala Thr Ala Glu Ala Lys Ala Ala Val Lys Thr
                485                 490                 495

Ala Lys Leu Ala Leu Asp Glu Ala Val Lys Ala Tyr Asn Asp Leu Thr
            500                 505                 510

Lys Glu Lys Gln Glu Gly Gln Glu Gly Lys Thr Ala Leu Ala Thr Val
    515                 520                 525

Asp Gln Lys Gln Lys Ala Tyr Asn Asp Ala Phe Val Lys Ala Asn Tyr
            530                 535                 540

Ser Tyr Glu Trp Val Ala Asp Lys Lys Ala Asp Asn Val Val Lys Leu
545                 550                 555                 560

Ile Ser Asn Ala Gly Gly Gln Phe Glu Ile Thr Gly Leu Asp Lys Gly
                565                 570                 575

Thr Tyr Ser Leu Glu Glu Thr Gln Val Pro Ala Gly Tyr Ala Thr Leu
            580                 585                 590

Ser Gly Asp Val Asn Phe Glu Val Thr Ala Thr Ser Tyr Ser Lys Gly
            595                 600                 605

Ala Thr Thr Asp Ile Ala Tyr Asp Lys Gly Ser Val Lys Lys Asp Ala
            610                 615                 620

Gln Gln Val Gln Asn Lys Lys Val Thr Ile Pro Gln Thr Gly Gly Ile
625                 630                 635                 640

Gly Thr Ile Leu Phe Thr Ile Ile Gly Leu Ser Ile Met Leu Gly Ala
                645                 650                 655

Val Val Val Met Lys Lys Arg Gln Ser Glu Glu Ala Tyr Pro Ala Phe
            660                 665                 670

Leu Tyr Lys Val Val Asp Ser Arg Leu Leu Thr Lys Pro Glu Arg Lys
            675                 680                 685

Leu Ser Trp Leu Leu Pro Pro Leu Ser Asn Asn
690                 695
```